(12) United States Patent
Bao et al.

(10) Patent No.: US 11,472,882 B2
(45) Date of Patent: Oct. 18, 2022

(54) ANTI-B7-H4 ANTIBODY, ANTIGEN-BINDING FRAGMENT THEREOF AND PHARMACEUTICAL USE THEREOF

(71) Applicants: JIANGSU HANSOH PHARMACEUTICAL GROUP CO., LTD., Jiangsu (CN); SHANGHAI HANSOH BIOMEDICAL CO., LTD., Shanghai (CN)

(72) Inventors: Rudi Bao, Jiangsu (CN); Haiqing Hua, Jiangsu (CN); Suxia Liu, Jiangsu (CN); Fujun Zhang, Jiangsu (CN); Ting Wang, Jiangsu (CN)

(73) Assignees: Jiangsu Hansoh Pharmaceutical Group Co., Ltd., Jiangsu (CN); Shanghai Hansoh Biomedical Co., Ltd., Shanghai (CN)

( * ) Notice: Subject to any disclaimer, the term of this patent is extended or adjusted under 35 U.S.C. 154(b) by 199 days.

(21) Appl. No.: 16/967,016

(22) PCT Filed: Feb. 1, 2019

(86) PCT No.: PCT/CN2019/074397
§ 371 (c)(1),
(2) Date: Aug. 3, 2020

(87) PCT Pub. No.: WO2019/154315
PCT Pub. Date: Aug. 15, 2019

(65) Prior Publication Data
US 2021/0032347 A1 Feb. 4, 2021

(30) Foreign Application Priority Data
Feb. 11, 2018 (CN) .......................... 201810142118.6

(51) Int. Cl.
| | | |
|---|---|---|
| *A61K 39/395* | (2006.01) | |
| *A61K 39/00* | (2006.01) | |
| *C07K 16/00* | (2006.01) | |
| *C07K 16/46* | (2006.01) | |
| *C07H 21/04* | (2006.01) | |
| *G01N 33/53* | (2006.01) | |
| *C12N 5/20* | (2006.01) | |
| *C12N 15/00* | (2006.01) | |
| *C07K 16/28* | (2006.01) | |

(52) U.S. Cl.
CPC .... *C07K 16/2827* (2013.01); *A61K 2039/505* (2013.01); *C07K 2317/565* (2013.01)

(58) Field of Classification Search
None
See application file for complete search history.

(56) References Cited

U.S. PATENT DOCUMENTS

| | | | | |
|---|---|---|---|---|
| 2003/0091580 A1* | 5/2003 | Mitcham | ............ | C07K 16/3069 435/69.3 |
| 2003/0124140 A1* | 7/2003 | Bangur | .............. | C07K 14/4748 435/69.3 |
| 2014/0322129 A1 | 10/2014 | Leong et al. | | |

FOREIGN PATENT DOCUMENTS

| | | |
|---|---|---|
| CN | 103981150 A | 8/2014 |
| CN | 104955475 A | 9/2015 |
| CN | 105189552 A | 12/2015 |
| CN | 107299085 A | 10/2017 |
| CN | 107531782 A | 1/2018 |
| WO | 2009073533 A2 | 6/2009 |
| WO | 2013025119 A1 | 2/2013 |

OTHER PUBLICATIONS

Annika C Sun et al, "B7-H4 as a protective shield for pancreatic islet beta cells," World Journal of Diabetes, vol. 5(6), pp. 739-746, Dec. 15, 2014.
In-Hak Choi et al, "Genomic Organization and Expression Analysis of B7-H4, an Immune Inhibitory Molecule of the B7 Family," The Journal of Immunology, vol. 171, pp. 4650-4654, Nov. 1, 2003.
"Human B7-H4 Alexa Fluor 488-conugated Antibody" R&D Systems, Monoclonal Mouse IgG2A Clone #973816, Catalog No. FAB65761G.
Ilona Kryczek et al, "B7-H4 expression identifies a novel suppressive macrophage population in human ovarian carcinoma," The Journal of Experimental Medicine, vol. 203, No. 4, Apr. 17, 2006, pp. 871-881.
Suh WK et al, Blood. Mol. Cell Biology. Sep. 2006, vol. 26 (17), pp. 6403-6411.
Sica GL et al, Immunity, Jun. 2003, vol. 18 (6), pp. 849-861 XXXXXXX.
Zhu G et al., Blood, Feb. 19, 2009, vol. 113(8), pp. 1759-1767 XXXXXXXX.
International Search Report dated Apr. 28, 2019 in corresponding application No. PCT/CN2019/074397.
Written Opinion dated Apr. 28, 2019 in corresponding application No. PCT/CN2019/074397.

(Continued)

*Primary Examiner* — Maher M Haddad
(74) *Attorney, Agent, or Firm* — Ice Miller LLP

(57) ABSTRACT

An anti-B7-H4 antibody, an antigen-binding fragment thereof and pharmaceutical use thereof. A chimeric antibody and a humanized antibody comprising a CDR region of the anti-B7-H4 antibody, a pharmaceutical composition comprising the anti-B7-H4 antibody and the antigen-binding fragment thereof, and use thereof as an anti-cancer medicament. A humanized anti-B7-H4 antibody and use thereof in the preparation of a medicament for treating diseases or conditions mediated by B7-H4.

21 Claims, 2 Drawing Sheets
Specification includes a Sequence Listing.

(56) References Cited

OTHER PUBLICATIONS

Zhang et al "Preparation and Characterization of Monoclonal Antibody Against Human B7-H4 Molecule" Monoclonal Antibodies in Immunodiagnosis and Immunotherapy, vol. 33, No. 4, Aug. 29, 2014 XXXXXXX.

Zhang, Biao et al "The Preparation of Anti-Human B7-H4 Monoclonal Antibody and Its Function Study" Chin J Hemorh, vol. 25, No. 1, Dec. 31, 2015, pp. 18-21 XXXXXXXX.

* cited by examiner

US 11,472,882 B2

ANTI-B7-H4 ANTIBODY, ANTIGEN-BINDING FRAGMENT THEREOF AND PHARMACEUTICAL USE THEREOF

CROSS-REFERENCE TO RELATED APPLICATION

This application is a Section 371 of International Application No. PCT/CN2019/074397, filed Feb. 1, 2019, which was published in the Chinese language on Aug. 15, 2019, under International Publication No. WO 2019/154315 A1, which claims priority under 35 U.S.C. § 119(b) to Chinese Application No. 201810142118.6, filed Feb. 11, 2018, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing" and a creation date of Jul. 27, 2020 and having a size of 76 kb. The sequence listing submitted via EFS-Web is part of the specification and is herein incorporated by reference in its entirety.

FIELD OF THE INVENTION

The present invention relates to an anti-B7-H4 antibody, antigen-binding fragment thereof, having immunoreactivity to human B7-H4 receptor, chimeric antibodies and humanized antibodies comprising the CDR regions of said anti-B7-H4 antibody, pharmaceutical compositions comprising the human anti-B7-H4 antibody and antigen-binding fragment thereof, and use thereof as anticancer agents.

BACKGROUND OF THE INVENTION

Tumor immunotherapy is a long-term research and development hotspot in the field of cancer treatment, and among which T cell tumor immunotherapy is in a central position. Tumor escape is a huge obstacle faced by tumor immunotherapy. Most expressing tumors can be recognized to varying degrees by the host immune system, but in many cases, tumor growth is promoted by the inhibition of the immune system caused by tumor cells per se, due to inadequate immune response triggered by inefficient activation of effector T cells. Tumor immunotherapy is to fully utilize and recruit killer T cells and/or other immune cells in tumor patients to kill tumors.

Studies on the CD28 receptor and its ligands have led to the characterization of related molecules known as the B7 superfamily. Members of the B7 family are a class of immunoglobulins with immunoglobulin V-like domain (IgV) and immunoglobulin C-like domain (IgC), members of which include costimulatory factors B7.1 (CD80) and B7.2 (CD86), inducible ligand for stimulatory factor (ICOS-L/B7-H2), programmed death-1 ligand (PD-L1/B7-H1), programmed death-2 ligand (PD-L2/B7-DC), B7-H4 and B7-H4, etc.

Human B7-H4 is a type I transmembrane protein consisting of 282 amino acids, the coding gene of which is located in the p11.1 region of chromosome 1 (Choi I H et al., J Immunol. 2003 Nov. 1; 171(9): 4650-4). B7-H4 plays a role in the negatively regulating T cell immune response. B7-H4 has extensively inhibitory effects on the differentiation, development, cell cycle progression and cytokine production of CD4+ and CD8+ T cells (Sica G L et al. Immunity. 2003 June; 18(6): 849-61). Immune cell disorders and autoimmune phenomena were not found in B7-H4 knockout mice (Zhu G et al, Blood. 2009 Feb. 19; 113(8): 1759-67; Suh W K et al., Blood. Mol Cell Biol. 2006 September; 26(17):6403-11). B7-H4 receptors and their signaling pathways are still unclear now.

Recent studies have found that B7-H4 protein is abundantly expressed in various tumor tissues, allowing tumor cells to escape from the attack of the body's immune system. As a target for tumor therapy, B7-H4 molecule provides a new method for tumor immunotherapy.

Currently, it is known that human B7-H4 is expressed on various cancer cells such as breast cancer, ovarian cancer, lung cancer, cervical cancer, kidney cancer, bladder cancer and liver cancer. B7-H4 mRNA expression was found in spleen, lung, thymus, liver, skeletal muscle, kidney, pancreas, testis and ovary. Low expression of B7-H4 at the protein level was found in tissues such as the breast (catheter and lobular), fallopian tube epithelium and endometrial gland. Related studies have also shown that B7-H4 is overexpressed in tumor-associated macrophages (TAM) (Kryczek, I. et al., J. Exp. Med. 2006, 203(4): 871-881), while macrophages constitute an important component of the tumor microenvironment and may account for up to 50% of tumor mass.

At present, numerous international pharmaceutical corporations are engaging in developing monoclonal antibodies against B7-H4 and/or drug-conjugates thereof to improve the patient's own immune system response to tumors and achieve direct killing of tumor cells. Related patents are, for example, WO2013025779, US20140322129 and the like. Anti-B7-H4 monoclonal antibodies available from companies such as Medimmune and FivePrime are currently being at pre-clinical phase; Genentech's anti-B7-H4 antibody-drug conjugates are also at preclinical development phase.

The present invention provides anti-B7-H4 antibodies with high affinity, high selectivity and high biological activity, for use in monoclonal antibody immunotherapy for tumors and related applications thereof. Medicaments, compositions, and methods for the treatment of B7-H4 positive tumors are also provided.

SUMMARY OF THE INVENTION

The present invention provides a B7-H4 antibody or antigen-binding fragment thereof, comprising:
antibody light chain variable region comprising at least one LCDR selected from the group consisting of:
SEQ ID NO: 6, SEQ ID NO: 7, SEQ ID NO: 8;
SEQ ID NO: 14, SEQ ID NO: 15, SEQ ID NO: 16;
SEQ ID NO:22, SEQ ID NO:23, SEQ ID NO:24;
SEQ ID NO:30, SEQ ID NO:31, SEQ ID NO:32;
SEQ ID NO:38, SEQ ID NO:39, SEQ ID NO:40;
SEQ ID NO:46, SEQ ID NO:47, SEQ ID NO:48;
SEQ ID NO:54, SEQ ID NO:55, SEQ ID NO:56;
SEQ ID NO: 62, SEQ ID NO: 63, SEQ ID NO: 64;
SEQ ID NO: 70, SEQ ID NO: 71, SEQ ID NO: 72; and
antibody heavy chain variable region comprising at least one HCDR selected from the group consisting of SEQ ID NO: 3, SEQ ID NO: 4, SEQ ID NO: 5;
SEQ ID NO: 11, SEQ ID NO: 12, SEQ ID NO: 13;
SEQ ID NO: 19, SEQ ID NO: 20, SEQ ID NO: 21;
SEQ ID NO: 27, SEQ ID NO: 28, SEQ ID NO: 29;
SEQ ID NO: 35, SEQ ID NO: 36, SEQ ID NO: 37;
SEQ ID NO: 43, SEQ ID NO: 44, SEQ ID NO: 45;

SEQ ID NO: 51, SEQ ID NO: 52, SEQ ID NO: 53;
SEQ ID NO: 59, SEQ ID NO: 60, SEQ ID NO: 61;
SEQ ID NO: 67, SEQ ID NO: 68, SEQ ID NO: 69;
SEQ ID NO: 73, SEQ ID NO: 74.

In a preferred embodiment of the invention, an anti-B7-H4 antibody or antigen-binding fragment thereof as described above is provided, wherein said antibody heavy chain variable region comprises:

HCDR1, HCDR2 and HCDR3 as shown in SEQ ID NO: 3, SEQ ID NO: 4 and SEQ ID NO: 5, respectively;

HCDR1, HCDR2 and HCDR3 as shown in SEQ ID NO: 11, SEQ ID NO: 12 and SEQ ID NO: 13, respectively;

HCDR1, HCDR2 and HCDR3 as shown in SEQ ID NO: 19, SEQ ID NO: 20 and SEQ ID NO: 21, respectively;

HCDR1, HCDR2 and HCDR3 as shown in SEQ ID NO: 27, SEQ ID NO: 28 and SEQ ID NO:29, respectively;

HCDR1, HCDR2 and HCDR3 as shown in SEQ ID NO: 35, SEQ ID NO: 36 and SEQ ID NO: 37, respectively;

HCDR1, HCDR2 and HCDR3 as shown in SEQ ID NO: 43, SEQ ID NO: 44 and SEQ ID NO: 45, respectively;

HCDR1, HCDR2 and HCDR3 as shown in SEQ ID NO: 51, SEQ ID NO: 52 and SEQ ID NO: 53, respectively;

HCDR1, HCDR2 and HCDR3 as shown in SEQ ID NO: 59, SEQ ID NO: 60 and SEQ ID NO: 61, respectively;

HCDR1, HCDR2 and HCDR3 as shown in SEQ ID NO: 67, SEQ ID NO: 68 and SEQ ID NO: 69, respectively; or HCDR1, HCDR2 and HCDR3 as shown in SEQ ID NO: 73, SEQ ID NO: 74 and SEQ ID NO: 21, respectively.

In a preferred embodiment of the invention, an anti-B7-H4 antibody or antigen-binding fragment thereof is provided, wherein said antibody light chain variable region comprises:

LCDR1, LCDR2 and LCDR3 as shown in SEQ ID NO: 6, SEQ ID NO: 7 and SEQ ID NO: 8, respectively;

LCDR1, LCDR2 and LCDR3 as shown in SEQ ID NO: 14, SEQ ID NO: 15 and SEQ ID NO: 16, respectively;

LCDR1, LCDR2 and LCDR3 as shown in SEQ ID NO: 22, SEQ ID NO: 23 and SEQ ID NO: 24, respectively;

LCDR1, LCDR2 and LCDR3 as shown in SEQ ID NO: 30, SEQ ID NO: 31 and SEQ ID NO: 32, respectively;

LCDR1, LCDR2 and LCDR3 as shown in SEQ ID NO: 38, SEQ ID NO: 39 and SEQ ID NO: 40, respectively;

LCDR1, LCDR2 and LCDR3 as shown in SEQ ID NO: 46, SEQ ID NO: 47 and SEQ ID NO: 48, respectively;

LCDR1, LCDR2 and LCDR3 as shown in SEQ ID NO: 54, SEQ ID NO: 55 and SEQ ID NO: 56, respectively;

LCDR1, LCDR2, and LCDR3 as shown in SEQ ID NO: 62, SEQ ID NO: 63, and SEQ ID NO: 64, respectively; or LCDR1, LCDR2, and LCDR3 as shown in SEQ ID NO: 70, SEQ ID NO: 71, and SEQ ID NO: 72, respectively.

A particularly preferred anti-B7-H4 antibody or antigen-binding fragment thereof may be any one selected from the group consisting of the followings, comprising one or more following CDR region sequence(s) or sequence(s) showing at least 95% sequence identity thereto:

(1) the antibody light chain variable region comprises LCDR1, LCDR2 and LCDR3 as shown in SEQ ID NO: 6, SEQ ID NO: 7 and SEQ ID NO: 8, respectively; and the antibody heavy chain variable region comprises HCDR1, HCDR2 and HCDR3 as shown in SEQ ID NO:3, SEQ ID NO:4 and SEQ ID NO:5, respectively;

(2) the antibody light chain variable region comprises LCDR1, LCDR2 and LCDR3 as shown in SEQ ID NO: 14, SEQ ID NO: 15 and SEQ ID NO: 16, respectively; and the antibody heavy chain variable region comprises HCDR1, HCDR2 and HCDR3 as shown in SEQ ID NO: 11, SEQ ID NO: 12 and SEQ ID NO: 13, respectively;

(3) the antibody light chain variable region comprises LCDR1, LCDR2 and LCDR3 as shown in SEQ ID NO: 22, SEQ ID NO: 23 and SEQ ID NO: 24, respectively; and the antibody heavy chain variable region comprises HCDR1, HCDR2 and HCDR3 as shown in SEQ ID NO: 19, SEQ ID NO: 20 and SEQ ID NO:21, respectively;

(4) the antibody light chain variable region comprises LCDR1, LCDR2 and LCDR3 as shown in SEQ ID NO: 30, SEQ ID NO: 31 and SEQ ID NO: 32, respectively; and the antibody heavy chain variable region comprises HCDR1, HCDR2 and HCDR3 as shown in SEQ ID NO:27, SEQ ID NO:28 and SEQ ID NO:29, respectively;

(5) the antibody light chain variable region comprises LCDR1, LCDR2 and LCDR3 as shown in SEQ ID NO: 38, SEQ ID NO: 39 and SEQ ID NO: 40, respectively; and the antibody heavy chain variable region comprises HCDR1, HCDR2 and HCDR3 as shown in SEQ ID NO: 35, SEQ ID NO: 36 and SEQ ID NO: 37, respectively;

(6) the antibody light chain variable region comprises LCDR1, LCDR2 and LCDR3 as shown in SEQ ID NO: 46, SEQ ID NO: 47 and SEQ ID NO: 48, respectively; and the antibody heavy chain variable region comprises HCDR1, HCDR2 and HCDR3 as shown in SEQ ID NO: 43, SEQ ID NO: 44 and SEQ ID NO: 45, respectively;

(7) the antibody light chain variable region comprises LCDR1, LCDR2 and LCDR3 as shown in SEQ ID NO: 54, SEQ ID NO: 55 and SEQ ID NO: 56, respectively; and the antibody heavy chain variable region comprises HCDR1, HCDR2 and HCDR3 as shown in SEQ ID NO: 51, SEQ ID NO: 52 and SEQ ID NO: 53, respectively;

(8) the antibody light chain variable region comprises LCDR1, LCDR2 and LCDR3 as shown in SEQ ID NO: 62, SEQ ID NO: 63 and SEQ ID NO: 64, respectively; and the antibody heavy chain variable region comprises HCDR1, HCDR2 and HCDR3 as shown in SEQ ID NO: 59, SEQ ID NO: 60 and SEQ ID NO: 61, respectively;

(9) the antibody light chain variable region comprises LCDR1, LCDR2 and LCDR3 as shown in SEQ ID NO: 70, SEQ ID NO: 71 and SEQ ID NO: 72, respectively; and the antibody heavy chain variable region comprises HCDR1, HCDR2 and HCDR3 as shown in SEQ ID NO: 67, SEQ ID NO: 68 and SEQ ID NO: 69, respectively; and

(10) the antibody light chain variable region comprises LCDR1, LCDR2 and LCDR3 as shown in SEQ ID NO: 22, SEQ ID NO: 23 and SEQ ID NO: 24, respectively; and the antibody heavy chain variable region comprises HCDR1, HCDR2 and HCDR3 shown in SEQ ID NO: 73, SEQ ID NO: 74 and SEQ ID NO: 21, respectively.

In a preferred embodiment of the invention, a B7-H4 antibody or antigen-binding fragment thereof as described above is provided, wherein the antibody or antigen-binding fragment thereof is a murine antibody or fragment thereof.

In a preferred embodiment of the invention, a B7-H4 antibody or antigen-binding fragment thereof is provided, wherein the antibody or antigen-binding fragment thereof is a chimeric antibody or fragment thereof.

In a preferred embodiment of the invention, an anti-B7-H4 antibody or antigen-binding fragment thereof as described above is provided, wherein the antibody or antigen-binding fragment thereof is a human antibody or fragment thereof.

In a preferred embodiment of the invention, a B7-H4 antibody or antigen-binding fragment thereof as described above is provided, wherein the antibody or antigen-binding fragment thereof is a humanized antibody or fragment thereof.

In a preferred embodiment of the invention, a B7-H4 antibody or antigen-binding fragment thereof as described above is provided, wherein the light chain variable region of the humanized antibody is light chain variable region comprising the sequence(s) selected from the group consisting of SEQ ID NO: 76, SEQ ID NO: 78, SEQ ID NO: 80 or SEQ ID NO: 82.

In a preferred embodiment of the invention, a B7-H4 antibody or antigen-binding fragment thereof as described above is provided, wherein the heavy chain variable region of the humanized antibody is heavy chain variable region comprising the sequence(s) selected from the group consisting of SEQ ID NO: 75, SEQ ID NO: 77, SEQ ID NO: 79 or SEQ ID NO: 81.

In a preferred embodiment of the invention, a B7-H4 antibody or antigen-binding fragment thereof as described above is provided, wherein the heavy chain variable region of the humanized antibody further comprises heavy chain constant region(s) of human IgG1, IgG2, IgG3 or IgG4 or a variant thereof, preferably comprises heavy chain constant region(s) of human IgG1, IgG2 or IgG4; more preferably comprises heavy chain constant region(s) of IgG1 which have been subjected to amino acid mutation to enhance ADCC toxicity.

In a preferred embodiment of the invention, a B7-H4 antibody or antigen-binding fragment thereof as described above is provided, wherein the light chain of the humanized antibody is light chain comprising the sequence selected from the group consisting of SEQ ID NO: 84, SEQ ID NO: 86, SEQ ID NO: 88 or SEQ ID NO: 90.

In a preferred embodiment of the invention, a B7-H4 antibody or antigen-binding fragment thereof as described above is provided, wherein the heavy chain of the humanized antibody is heavy chain comprising the sequence selected from the group consisting of SEQ ID NO: 83 SEQ ID NO: 85, SEQ ID NO: 87 or SEQ ID NO: 89.

In a preferred embodiment of the invention, a B7-H4 antibody or antigen-binding fragment thereof as described above is provided, wherein the light chain variable region of the humanized antibody is light chain variable region comprising the sequence selected from the group consisting of SEQ ID NO: 76 or SEQ ID NO: 80.

In a preferred embodiment of the invention, a B7-H4 antibody or antigen-binding fragment thereof as described above is provided, wherein the heavy chain variable region of the humanized antibody is heavy chain variable region comprising the sequence selected from the group consisting of SEQ ID NO: 75 or SEQ ID NO: 79 In a preferred embodiment of the invention, a B7-H4 antibody or antigen-binding fragment thereof as described above is provided, wherein the light chain of the humanized antibody comprising the sequence selected from the group consisting of SEQ ID NO: 84 or SEQ ID NO: 88.

In a preferred embodiment of the invention, a B7-H4 antibody or antigen-binding fragment thereof as described above is provided, wherein the heavy chain of the humanized antibody comprising the sequence selected from the group consisting of SEQ ID NO: 83 or SEQ ID NO:87.

In a more preferred embodiment of the invention, the humanized antibody is selected from any of the following antibodies comprising:
(1) light chain variable region of SEQ ID NO: 76 and heavy chain variable region of SEQ ID NO: 75;
(2) light chain variable region of SEQ ID NO: 78 and a heavy chain variable region of SEQ ID NO: 77;
(3) light chain variable region of SEQ ID NO: 80 and heavy chain variable region of SEQ ID NO: 79; or
(4) light chain variable region of SEQ ID NO: 82 and heavy chain variable region of SEQ ID NO: 81.

In a further preferred embodiment of the invention, the humanized antibody is selected from any one of the following antibodies comprising:
(1) light chain of SEQ ID NO: 84 and heavy chain of SEQ ID NO: 83;
(2) light chain of SEQ ID NO: 86 and heavy chain of SEQ ID NO: 85;
(3) light chain of SEQ ID NO: 88 and heavy chain of SEQ ID NO: 87; or
(4) light chain of SEQ ID NO: 90 and heavy chain of SEQ ID NO: 89.

An anti-B7-H4 antibody or antigen-binding fragment thereof, having at least one of the following characteristics: (1) binding to an epitope comprising amino acids 41-60 in SEQ ID NO: 100 of B7-H4; and (2) binding to an epitope comprising amino acids 53-59 in SEQ ID NO: 100 of B7-H4.

An anti-B7-H4 antibody or antigen-binding fragment thereof, having at least one of the following characteristics: (1) binding to an epitope comprising amino acid 53 in SEQ ID NO: 100 of B7-H4; (2) binding to an epitope comprising amino acid 54 in SEQ ID NO: 100 of B7-H4; (3) binding to an epitope comprising amino acid 56 in SEQ ID NO: 100 of B7-H4; (4) binding to an epitope comprising amino acid 57 in SEQ ID NO: 100 of B7-H4; (5) binding to an epitope comprising amino acid 58 in SEQ ID NO: 100 of B7-H4; and (2) binding to an epitope comprising amino acid 59 in SEQ ID NO: 100 of B7-H4.

In a preferred embodiment of the invention, a B7-H4 antibody or antigen-binding fragment thereof as described above is provided, wherein the antigen-binding fragment is Fab, Fv, sFv, F(ab')$_2$, linear antibody, single-chain antibody, nanobody, domain antibody, or multispecific antibody.

The present invention further provides a DNA sequence encoding the B7-H4 antibody or antigen-binding fragment thereof as described above.

The present invention further provides an expression vector comprising the DNA sequence as described above.

The invention further provides a host cell transformed with or comprising the expression vector as described above.

In a preferred embodiment of the invention, the host cell as described above is characterized in that the host cell is bacterium, preferably *Escherichia coli*.

In a preferred embodiment of the invention, the host cell as described above is yeast, preferably *Pichia pastoris*.

In a preferred embodiment of the invention, the host cell as described above is mammalian cell, preferably Chinese hamster ovary (CHO) cell or human embryonic kidney (HEK) 293 cell.

The invention also provides a method of producing the B7-H4 antibody, including culturing the host cell as described above, isolating the antibody from the culture, and purifying the antibody.

The invention also provides a multispecific antibody comprising the light chain variable region and the heavy chain variable region as described above.

The invention also provides a single chain antibody comprising the light chain variable region and the heavy chain variable region as described above.

The invention also provides a detection reagent or diagnostic agent comprising the B7-H4 antibody or antigen-binding fragment thereof as described above.

The present invention also provides a method for immunodetection or measurement of B7-H4, which comprises using the B7-H4 antibody or antigen-binding fragment thereof of the present invention.

The present invention also provides a method for diagnosing diseases associated with B7-H4 positive cells, the method comprises detecting or measuring B7-H4 or B7-H4 positive cells by using the B7-H4 antibody or antigen-binding fragment thereof according to the present invention.

The invention further provides a pharmaceutical composition comprising the B7-H4 antibody or antigen-binding fragment thereof as described above and a pharmaceutically acceptable excipient, dilution or carrier.

The present invention further provides use of the anti-B7-H4 antibody or antigen-binding fragment thereof as described above in the manufacture of a medicament for the treatment of B7-H4 mediated disease or condition; wherein the disease is preferably a cancer; preferably, the disease is B7-H4 expressing cancer; the cancer is most preferably selected from the group consisting of breast cancer, ovarian cancer, prostate cancer, pancreatic cancer, kidney cancer, lung cancer, liver cancer, stomach cancer, colon cancer, bladder cancer, esophageal cancer, cervical cancer, gallbladder cancer, glioblastoma and melanoma.

The present invention further provides a method of treating and preventing B7-H4 mediated diseases or conditions, including administering to a subject in need thereof a therapeutically effective amount of the anti-B7-H4 antibody or antigen-binding fragment thereof, or a pharmaceutical composition comprising the same, wherein the disease is preferably a cancer; preferably, the disease is B7-H4 expressing cancer; the cancer is most preferably selected from the group consisting of breast cancer, ovarian cancer, prostate cancer, pancreatic cancer, kidney cancer, lung cancer, liver cancer, stomach cancer, colon cancer, bladder cancer, esophageal cancer, gallbladder cancer, cervical cancer, glioblastoma and melanoma.

DETAILED DESCRIPTION OF THE DISCLOSURE

1. Terminology

Figure 1:
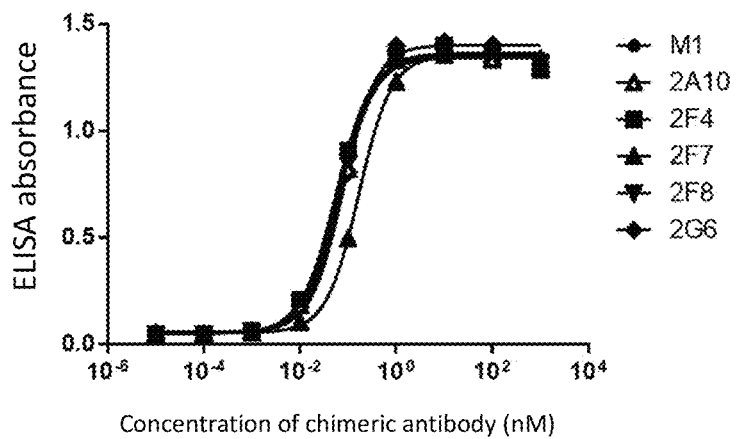
FIG. 1: in vitro ELISA binding assay of antibodies, showing that all seven chimeric antibodies have binding activity to the purified human B7-H4 antigen, wherein the chimeric antibodies 2F7 and 2F8 have $EC_{50}$ of about 0.1 nM.

In order to more readily understand the invention, certain technical and scientific terms are specifically defined below. Unless specifically defined elsewhere in this document, all other technical and scientific terms used herein have the meaning commonly understood by one of ordinary skill in the art to which this invention pertains.

As used herein, the single-letter code and the three-letter code for amino acids are as described in J. biol. chem, 243, (1968) p 3558.

As used herein, the term "antibody" refers to immunoglobulin, a four-peptide chain structure formed by connecting two identical heavy chains and two identical light chains together by interchain disulfide bond(s). Different immunoglobulin heavy chain constant regions exhibit different amino acid compositions and sequences, thereby presenting different antigenicity. Accordingly, immunoglobulins can be divided into five categories, or called immunoglobulin isotypes, namely IgM, IgD, IgG, IgA and IgE, their heavy chains are p chain, 6 chain, y chain, a chain and E chain, respectively. According to its amino acid composition of hinge region and the number and location of heavy chain disulfide bonds, the same type of Ig can be divided into different sub-categories, for example, IgG can be divided into IgG1, IgG2, IgG3, and IgG4. Light chain can be divided into κ or λ chain according to different constant regions. Each of the five Igs can have κ or λ chain.

In the present invention, the antibody light chain variable region described herein further comprises a light chain constant region, which comprises a human or murine κ, λ chain or a variant thereof.

In the present invention, the antibody heavy chain variable region described herein further comprises a heavy chain constant region, which comprises human or murine IgG1, 2, 3, 4 or a variant thereof.

The sequences of about 110 amino acids located near the N-terminal of the antibody heavy chains and light chains, vary largely, this region is known as variable region (V region); the rest of the amino acid sequence near the C-terminus is relative stable, known as constant region (C region). Variable region comprises three hypervariable regions (HVR) and four relatively conserved sequence framework region (FR). The three hypervariable regions determine the specificity of the antibody, also known as complementarity determining region (CDR). Each light chain variable region (LCVR) and each heavy chain variable region (HCVR) are consisted of three CDRs and four FRs, from the amino terminal to the carboxyl terminal being: FR1, CDR1, FR2, CDR2, FR3, CDR3, and FR4. Three light chain CDRs refer to LCDR1, LCDR2, and LCDR3; three heavy chain CDRs refer to HCDR1, HCDR2 and HCDR3. The numbers and locations of CDR amino acid residues in VL and VH of the antibody or antigen-binding fragment herein comply with the known Kabat numbering criteria and Kabat or AbM definition criteria (http://bioinf.org.uk/abs/).

The term "antigen presenting cell" or "APC" is a cell that displays on its surface foreign antigens complexed with MHC. T cells recognize such complex by T cell receptors (TCRs). Examples of APCs include, but are not limited to, dendritic cells (DC), peripheral blood mononuclear cells (PBMCs), monocytes, B lymphoblasts and monocyte-derived dendritic cells (DC). The term "antigen presentation" refers to a process during which APCs capture antigens and allow them to be recognized by T cells, for example as a component of MHC-I/MHC-II conjugates.

The term "B7-H4" refers to a member of the human B7 protein family, also known as CD276, which is a type I transmembrane protein having four Ig-like extracellular domains. B7-H4 is one of the immune checkpoint proteins expressed on the surface of antigen-presenting cells or cancer cells, and it has an inhibitory effect on activation of T cells. The term "B7-H4" includes any variant or isoform of B7-H4 naturally expressed by cells. The antibodies of the present invention can cross-react with B7-H4 obtained from non-human species. Alternatively, the antibodies may be specific for human B7-H4, and may not exhibit cross-reactivity with other species. B7-H4 or any variant or isotype thereof can be isolated from cells or tissues in which they are naturally expressed, or produced by recombinant techniques using techniques commonly used in the art and those described herein. Preferably, the anti-B7-H4 antibodies target human B7-H4 with normal glycosylation pattern.

The term "recombinant human antibody" includes human antibodies prepared, expressed, created or isolated by recombinant methods, and the techniques and methods involved are well known in the art, such as: (1) an antibody isolated from a human immunoglobulin gene transgenic or transchromosomal animal (e.g., a mouse), or a prepared hybridoma; (2) an antibody isolated from transformed host cells expressing the antibody, such as a transfectoma; (3) an antibody isolated from a recombinant combinatorial human antibody library; and (4) an antibody prepared, expressed, created or isolated by splicing human immunoglobulin gene sequences onto other DNA sequences or the like. Such recombinant human antibody comprises variable region and constant region by incorporating specific human germline immunoglobulin sequences encoded by germline genes, but also subsequent rearrangements and mutations such as those occurred during the antibody maturation.

The term "murine antibody" in the present invention refers to anti-human B7-H4 monoclonal antibody prepared according to the knowledge and skills in the art. During the preparation, a test object is injected with B7-H4 antigen, and then hybridoma expressing antibody which possesses desired sequence or functional characteristics is isolated. In a preferred embodiment of the present application, the murine B7-H4 antibody or the antigen-binding fragment thereof further comprises a light chain constant region of murine κ, λ chain or a variant thereof, or further comprises a heavy chain constant region of murine IgG1, IgG2, IgG3 or IgG4, or a variant thereof.

The term "human antibody" includes antibodies having variable and constant regions from human germline immunoglobulin sequences. Human antibodies of the present invention may include amino acid residues that are not encoded by human germline immunoglobulin sequences (e.g., mutations introduced by random or site-specific mutagenesis in vitro or by somatic mutation in vivo). However, the term "human antibody" does not include an antibody in which CDR sequences derived from other mammalian species germline, such as mouse germline, have been grafted onto a human framework sequence (i.e., "humanized antibody").

The term "humanized antibody", also known as CDR-grafted antibody, refers to an antibody generated by grafting murine CDR sequences into a variable region framework of human antibody. Humanized antibodies avoid the undesired strong antibody response induced by the chimeric antibodies which carry a large amount of murine protein components. To avoid a decrease in the activity caused by the reduced immunogenicity, the variable region of the human antibody can be subjected to a minimum back mutation to maintain the activity.

The term "chimeric antibody", is an antibody which is formed by fusing the variable region of a murine antibody with the constant region of a human antibody, and the chimeric antibody can alleviate the murine antibody-induced immune response. To establish a chimeric antibody, hybridoma secreting specific murine monoclonal antibody is firstly established, a variable region gene is cloned from mouse hybridoma cells, then a constant region gene of a human antibody is cloned as desired, the mouse variable region gene is ligated with the human constant region gene to form a chimeric gene which then can be inserted into a human vector, and finally the chimeric antibody molecule is expressed in eukaryotic or prokaryotic industrial system.

The constant region of a human antibody is selected from the heavy chain constant region of human IgG1, IgG2, IgG3 or IgG4 or a variant thereof, preferably is the heavy chain constant region of human IgG2 or IgG4, or the heavy chain constant region of IgG1 which exhibits increased ADCC (antibody-dependent cell-mediated cytotoxicity), due to amino acid mutation.

The term "antigen-binding fragment" refers to antigen-binding fragments of an antibody and analogs of an antibody, which generally include at least a part of the antigen-binding region or variable region (e.g., one or more CDRs) of the parental antibody. Antibody fragments retain at least some of the binding specificity of the parent antibody. Generally, when the activity is expressed as molar, antibody fragments retain at least 10% binding activity of the parental antibody. Preferably, the antibody fragments retain at least 20%, 50%, 70%, 80%, 90%, 95%, or 100% or more binding affinity of the parental antibody to the target. Examples of antigen-binding fragments include, but are not limited to Fab, Fab', F(ab')2, Fv fragments, linear antibodies, single chain antibodies, nanobodies, domain antibodies, and multispecific antibodies. Engineered antibody variants are reviewed in Holliger and Hudson (2005) Nat. Biotechnol. 23: 1126-1136.

"Fab fragment" is composed of a light chain, a heavy chain CH1 and variable regions. The heavy chain of a Fab molecule cannot form disulfide bond with another heavy chain molecule.

"Fc" region contains two heavy chain fragments comprising the antibody CH1 and CH2 domains. The two heavy chain fragments are held together by two or more disulfide bonds and hydrophobic interaction of the CH3 domain.

"Fab' fragment" contains a light chain and part of a heavy chain comprising VH domain, CH1 domain and a region between the CH1 and CH2 domains, and thereby a F(ab')2 molecule can be formed by two heavy chains of two Fab' fragments linked by interchain disulfide bonds.

"F(ab')2 fragment" contains two light chains and part of heavy chains comprising the constant region between CH1 and CH2 domains, thereby interchain disulfide bonds are formed between the two heavy chains. Therefore, the F(ab')2 fragment consists of two Fab' fragments held together by disulfide bonds between the two heavy chains.

"Fv region" contains variable regions from both heavy and light chains, but without constant regions.

The term "multispecific antibody" is used in its broadest sense and encompasses antibodies with multi-epitope specificity. These multispecific antibodies include, but are not limited to antibodies comprising a heavy chain variable region (VH) and a light chain variable region (VL), where the VH-VL unit has multiple epitope specificity; antibodies comprising two or more VL and VH regions, where each VH-VL unit binds to different targets or to different epitopes of the same target; antibodies comprising two or more single variable regions, where each single variable region binds to different targets or to different epitopes of the same target; full-length antibodies; antibody fragments; diabodies; bispecific diabodies and triabodies, antibody fragments which have been covalently or non-covalently linked together.

The term "single-chain antibody" is a single-chain recombinant protein composed of antibody heavy chain variable region (VH) and light chain variable region (VL) connected by a peptide linker, and the single-chain antibody is the smallest antibody fragment with intact antigen binding sites.

The term "domain antibody fragment" is an immunoglobulin fragment having immunological functions and it only contains heavy chain variable region or light chain variable region chain. In some cases, two or more VH regions are covalently linked to a peptide linker to form a bivalent domain antibody fragment. The two VH regions of a bivalent domain antibody fragment can target the same or different antigens.

The term "binding to B7-H4", refers to the interaction with human B7-H4. The term "antigen binding site" as used herein refers to discontinuous three-dimensional sites on the antigen, recognized the antibody or the antigen-binding fragment of the present application.

The term "epitope" refers to the sites on an antigen that specifically bind to an immunoglobulin or antibody. The epitope can be formed by adjacent amino acids, or by non-adjacent amino acids but brought to be closed due to tertiary folding of a protein.

The epitope formed by adjacent amino acids is typically retained after exposure to denaturing solvents, whereas the epitope formed by tertiary folding is typically lost after treatment with denaturing solvents. Epitopes typically include at least 3-15 amino acids in a unique spatial conformation. Methods for determining what epitope is bound by a given antibody are well known in the art, including immunoblotting and immunoprecipitation assays, and the like. Methods for determining the spatial conformation of an epitope include techniques in the art and techniques described herein, such as X-ray crystallography and two-dimensional nuclear magnetic resonance.

The term "specifically binds to", "selectively binds to" as used herein, refers to the binding of an antibody to an epitope on a predetermined antigen. Typically, where a recombinant human B7-H4 is used as analyte and an antibody is used as ligand, the antibody binds to a predetermined antigen at approximately less than $10^{-7}$ M or even less equilibrium dissociation constant ($K_D$), and the affinity of the antibody for binding to the predetermined antigen is at least two times higher than that for non-specific antigens (other than the predetermined antigen or closely related antigens) (such as BSA), as measured in an instrument via surface plasmon resonance (SPR) techniques. The term "an antibody which recognizes the antigen" can be used interchangeably herein with the term "specifically binding antibody".

The term "cross reaction" refers to the ability of the antibody of the present invention to bind to B7-H4 derived from different species. For example, an antibody of the present invention that binds to human B7-H4 can also bind to B7-H4 derived from another species. Cross-reactivity is measured by detecting the specific reactivity with purified antigen in binding assays (e.g., SPR and ELISA), or by detecting the binding or functional interaction with cells physiologically expressing B7-H4. Methods for determining cross-reactivity include standard binding assays as described herein, such as surface plasmon resonance (SPR) analysis, or flow cytometry.

The terms "inhibition" or "blockade" are used interchangeably and encompass both partial and complete inhibition/blockade. Inhibition/blockade of ligand preferably reduces the normal ligand-binding level or alters type of ligand-binding activity, when compared with that in the absence of inhibition or blockade. Inhibition and blockade are also intended to include any measurable decrease in binding affinity where a ligand is contacted with an anti-B7-H4 antibody, when compared with the binding affinity in the absence of anti-B7-H4 antibody.

The term "inhibiting the growth" (e.g., in the context of cells) is intended to include any measurable reduction in cell growth.

The terms "inducing an immune response" and "enhancing an immune response" are used interchangeably and refer to the stimulation of a particular antigen (i.e., passive or adaptive). With respect to the induction of CDC or ADCC, the term "inducing" means to stimulate a specific mechanism to directly kill cells.

As used herein, the term "ADCC", namely antibody-dependent cell-mediated cytotoxicity, refers to cells expressing Fc receptors directly kill target cells coated by an antibody through recognizing the Fc segment of the antibody. ADCC effector function of the antibody can be reduced or eliminated via modification of the Fc segment of IgG. The modification refers to mutation(s) of the antibody heavy chain constant region.

Methods for producing and purifying antibodies and antigen-binding fragments are well known in the art and can be found, for example, in Using Antibodies A Laboratory Manual Cold Spring Harbor, Chapter 5-8 and 15. For example, mice can be immunized with human B7-H4, or fragments thereof, and the resulting antibodies can then be renatured, purified and sequenced using conventional methods well known in the art. Antigen-binding fragments can also be prepared by conventional methods. The antibody or the antigen-binding fragment of the present invention can be obtained by introducing one or more human framework regions (FRs) into non-human derived CDRs using genetic engineering. Human FR germline sequences can be obtained from ImMunoGeneTics (IMGT) on website http://imgt.cines.fr, or from The Immunoglobulin FactsBook, 2001 ISBN012441351.

The engineered antibody or antigen-binding fragment of the present invention may be prepared and purified using conventional methods. For example, cDNA sequences encoding corresponding antibodies may be cloned and recombined into a GS expression vector. The recombined immunoglobulin expression vector may then be stably transfected into CHO cells. As a more recommended method well known in the art, mammalian expression systems may result in glycosylation of antibodies, typically at the highly conserved N-terminus in the Fc region. Stable clones may be obtained through expression of an antibody specifically binding to human antigen. Positive clones may be expanded in a serum-free culture medium for antibody production in bioreactors. Culture medium, into which an antibody has been secreted, may be purified and collected by conventional techniques. The antibody may be filtered and concentrated using common techniques. Soluble mixtures and aggregates may be effectively removed by common techniques, such as molecular sieve or ion exchange. The resulting product should be immediately frozen, for example at −70° C., or may be lyophilized.

The antibodies of the present invention refer to monoclonal antibodies. Monoclonal antibody or mAb, as used herein, refers to an antibody that is derived from a single clone including but is not limited to eukaryotic, prokaryotic, or phage single clone strain. Monoclonal antibodies or antigen-binding fragments thereof can be obtained, for example, by hybridoma technologies, recombinant technologies, phage display technologies, synthetic technologies (e.g., CDR-grafting), or other technologies known in the art.

"Administration" and "treatment," as it applies to an animal, human, experimental subject, cell, tissue, organ, or biological fluid, refers to contacting an exogenous pharmaceutical, therapeutic, diagnostic agent, or composition with the animal, human, subject, cell, tissue, organ, or biological fluid. "Administration" and "treatment" can refer, e.g., to therapeutic, pharmacokinetic, diagnostic, research, and experimental methods. Treatment of a cell encompasses contacting a reagent with the cell, as well as contacting a reagent with a fluid, where the fluid is in contact with the cell. "Administration" and "treatment" also mean in vitro and ex vivo treatments, e.g., of a cell, by a reagent, diagnostic, binding composition, or by another cell. "Treatment", as it applies to a human, veterinary, or a research subject, refers to therapeutic treatment, prophylactic or preventative measures, research and diagnostic applications.

"Treat" means to administer a therapeutic agent, such as a composition comprising any of the binding compounds of the present invention, internally or externally to a patient suffering from one or more disease symptoms for which the agent has known therapeutic activity. Typically, the therapeutic agent is administered in an amount effective to alleviate one or more disease symptoms in the treated patient or population, either by inducing the regression of symptom(s) or by inhibiting the progression of such symptom(s) to any clinically measurable degree. The amount of a therapeutic agent that is effective to alleviate any particular disease symptom (also referred to "therapeutically effective amount") may vary according to factors such as the disease state, age, and weight of the patient, and the ability of the agent to elicit a desired response in the patient. Whether a disease symptom has been alleviated can be assessed by any clinical measurement typically used by physicians or other skilled healthcare providers to assess the severity or progression status of that symptom. While an embodiment (e.g., a treatment method or article of manufacture) of the present invention may not be effective in alleviating the target disease symptom(s) of interest in each patient, it should alleviate the target disease symptom(s) of interest in a statistically significant number of patients as determined by any statistical test known in the art such as the Student's t-test, chi-square test, U-test according to Mann and Whitney, Kruskal-Wallis test (H-test), Jonckheere-Terpstra-test and the Wilcoxon-test.

The term "consisting essentially of" or variations thereof used throughout the specification and claims means to involve all the elements or groups of elements, and optionally other elements showing similar property or even different property from that of said elements. Said other elements do not significantly change the substantial or novel property of the given dosing regimen, method, or composition. As a non-limiting example, a binding compound consisting essentially of the described amino acid sequence may also include one or more amino acid(s), which do not significantly affect the properties of the binding compound.

The term "naturally occurring" as applied to an object in the present invention is refers to the fact that the object can be found in nature. For example, polypeptide sequences or polynucleotide sequences that exist in organisms (including viruses) and have not been artificially modified in the laboratory are naturally occurring, wherein said organism can be isolated from natural sources.

"Effective amount" encompasses an amount sufficiently to ameliorate or prevent a symptom or sign of a medical condition. Effective amount also means an amount sufficiently to allow or facilitate diagnosis. An effective amount for a particular patient or veterinary subject may vary depending on factors such as the condition being treated, the general health of the patient, the route and dose of administration and the severity of side effects. An effective amount can be the maximal dose or dosing protocol that avoids significant side effects or toxic effects.

"Exogenous" refers to substances that are produced outside an organism, cell, or human body, depending on the context. "Endogenous" refers to substances that are produced within a cell, organism, or human body, depending on the context.

"Homology" refers to sequence similarity between two polynucleotide sequences or between two polypeptides. When a position within two sequences to be compared is occupied by the same base or amino acid monomer subunit, e.g., if a position within each of two DNA molecules is occupied by adenine, then the molecules are homologous at this position. The percentage of homology between two sequences is a function, in which the number of matching or homologous positions shared by the two sequences is divided by the number of positions to be compared, and then multiplied by 100. For example, if 6 out of 10 positions in two sequences are matched or homologous when the sequences are optimally aligned, then the two sequences are deemed as 60% homologous. Generally, the comparison is performed, when two sequences are aligned to give maximum homology percentage.

As used herein, the expressions "cell," "cell line," and "cell culture" are used interchangeably and all such designations include progeny thereof. Thus, the wordings "transformants" and "transformed cells" include the primary subject cell and cultures derived therefrom without considering the number of passages. It should also be understood that all progenies may not be precisely identical in DNA content, due to intended or unintended mutations. Mutant progenies thus screened that exhibit the same function or biological activity as that of originally transformed cell are also taken into consideration. Where distinct designations are intended, it will be obvious from the context.

"Optional" or "optionally" means that the event or circumstance that follows may but not necessarily happen, and the description includes the instance in which the event or circumstance shall or shall not happen. For example, "optionally comprises 1-3 antibody heavy chain variable regions" means the antibody heavy chain variable region having specific sequence may be, but not necessarily be present.

"Pharmaceutical composition" refers to a mixture comprising one or more compound(s) according to the present invention or a physiologically/pharmaceutically acceptable salt or prodrug thereof, along with other chemical components, as well as additional components such as physiologically/pharmaceutically acceptable carriers and excipients. The pharmaceutical composition aims at promoting the administration to an organism, facilitating the absorption of the active ingredient and thereby exerting a biological effect.

Hereinafter, the present invention is further described with reference to examples; however, the scope of the present invention is not limited thereto. In the examples of the present invention, where specific conditions are not described, the experiments are generally conducted under conventional conditions as described in Antibodies A Laboratory Manual, Molecular Cloning, Cold Spring Harbor, or under conditions proposed by the material or product manufacturers. Where the source of the reagents is not specifically provided, the reagents are commercially available conventional reagents.

Example 1: Preparation of Antigens and Construction of Stable Cell Lines

Sequence encoding Human B7-H4 with HisFlag tag (huB7-H4-HF), and sequence encoding human B7-H4 with huFc tag (h-B7-H4-Fc) were synthesized by CRO Integrated DNA Technology (IDT) (the template sequence for each of the above B7-H4 recombinant proteins was designed by the inventors), and were cloned into pTT5 vector (Biovector) respectively. The B7-H4 recombinant proteins were expressed in 293T cells and purified according to Example 2.

The purified proteins were used in the following examples.

huB7-H4-Fc sequence:
SEQ ID NO: 99
FGISGRHSITVTTVASAGNIGEDGILSCTFEPDIKLSDIVIQWLKEGVLG

LVHEFKEGKDELSEQDEMFRGRTAVFADQVIVGNASLRLKNVQLTDAGTY

KCYIITSKGKGNANLEYKTGAFSMPEVNVDYNASSETLRCEAPRWFPQPT

VVWASQVDQGANFSEVSNTSFELNSENVTMKVVSVLYNVTINNTYSCMIE

NDIAKATGDIKVTESEIKRRSHLQLLNSKAGSGGGGDKTHTCPPCPAPEL

LGGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHN

HYTQKSLSLSPGK huB7-H4-his sequence:
SEQ ID NO: 100
MASLGQILFWSIISIIILAGAIALIIGFGISGRHSITVTTVASAGNIGE

DGILSCTFEPDIKLSDIVIQWLKEGVLGLVHEFKEGKDELSEQDEMFRGR

TAVFADQVIVGNASLRLKNVQLTDAGTYKCYIITSKGKGNANLEYKTGAF

SMPEVNVDYNASSETLRCEAPRWFPQPTVVWASQVDQGANFSEVSNTSFE

LNSENVTMKVVSVLYNVTINNTYSCMIENDIAKATGDIKVTESEIKRRSH

LQLLNSKADYKDDDDKGSHHHHHHHH

Purification Steps for huB7-H4-his:

The supernatant samples expressed by cells were centrifuged at high speed to remove impurities, subjected to buffer exchange with PBS, and added with imidazole to a final concentration of 5 mM. The nickel column was equilibrated with PBS solution comprising 5 mM imidazole and rinsed with 2-5 column volumes. After buffer exchange, the supernatant samples were applied to the column. The column was washed with PBS comprising 5 mM imidazole until the A280 reading returned to baseline. The column was then washed with PBS+10 mM imidazole, the non-specifically bound impurity proteins were removed, and the effluent was collected. The target protein was eluted with PBS comprising 300 mM imidazole, and the elution peak was collected. The collected eluate was further purified by ion exchange (SP column). Stock Solution A: 0.01 M PB, pH 8.0. Stock Solution B: Solution A+1 M NaCl. For the target protein elution, the PBS-imidazole solution was replaced with Solution A, and the SP column was equilibrated with solution A. And then, the samples were applied onto the column. The column was then washed with Solution B at a concentration gradient from 0 to 100%, with 10 column volumes, and the elution peak was collected. The resulting protein was identified as desired protein via electrophoresis, and aliquoted for use. Human B7-H4 with the HisFlag tag (hu-B7-H4 his) was obtained.

Purification Steps for huB7-H4-Fc:

The supernatant samples expressed by HEK293 cells were centrifuged at high speed to remove impurities, and subjected to buffer exchange with PBS. The Protein A affinity column was equilibrated with 10 mM phosphate buffer, and rinsed with 2-5 column volumes. After buffer exchange, the supernatant samples were applied onto the column. The column was rinsed with buffer at 25 column volumes until the A280 reading returned to the baseline. The target protein was eluted with 0.8% acetate buffer, pH 3.5, and the elution peak was collected. The aliquots were immediately added with 1M Tris-Cl buffer, pH 8.0 for neutralization. And then the solution was exchanged with PBS via Millipore's Amico-15 filter column. The resulting protein was identified by electrophoresis, peptide mapping and LC-MS, and aliquoted for use.

Construction of Stable CHO-S Cell Pool:

The full-length sequence encoding human or cynomolgus B7-H4 protein (huB7-H4 or cyB7-H4) was synthesized by Integrated DNA Technology (IDT) (the above B7-H3 recombinant proteins were designed by the present inventors) and was cloned into engineered pcDNA3.1 vector, pcDNA3.1/puro (Invitrogen #V79020), respectively. CHO-S(ATCC) cells were cultured in CD-CHO culture medium (Life Technologies, #10743029) to reach $0.5 \times 10^6$/ml. 10 μg of the vector encoding the huB7-H4 or cyB7-H4 gene was mixed with 50 μl of LF-LTX (Life Technologies, #A12621) in 1 ml Opti-MEM medium (Life Technologies, #31985088), incubated at room temperature for 20 minutes, added into culture medium of CHO cells, and placed in an incubator with $CO_2$ for cultivation. After 24 hours, the medium was changed with fresh medium and 10 μg/ml puromycin was added. After that, the culture medium was changed every 2-3 days, and stable CHO-S cell pool was obtained after 10-12 day by screening.

Example 2: Obtaining Murine Hybridomas and Antibody Sequences

Animals were immunized with human antigen huB7-H4-Fc. Five Balb/c and five A/J mice (female, 10 weeks old) were used. The immunogen and the immunoadjuvant (Sigma Complete Freund's Adjuvant (CFA) or Sigma Incomplete Freund's Adjuvant (IFA)) were thoroughly mixed at a ratio of 1:1 and emulsified to prepare a stable "water-in-oil" liquid; The dose for injection was 25 μg/200 L/mouse.

| Day 1 | first immunization, CFA |
|---|---|
| Day 21 | second immunization, IFA |
| Day 35 | third immunization, IFA |
| Day 42 | Blood collection and detection of serum titer (blood collected after three times of immunization) |
| Day 49 | forth immunization, IFA |
| Day 56 | Blood collection and detection of serum titer (blood collected after four times of immunization) |

Serum titer and the ability to bind to cell surface antigens were evaluated with sera from the immunized mice by indirect ELISA and Capture ELISA method as described in Example 3. Cell fusion was initiated depending on the results of the titer assay (greater than 100,000-fold dilution). The mice with strong serum titer, affinity and FACS binding were subjected to a final immunization and then were sacrificed. Spleen cells and SP2/0 myeloma cells were fused and plated onto the plate to obtain hybridomas, which was screened by indirect ELISA and capture ELISA to obtain target hybridomas. Monoclonal cell strains were established by limiting dilution. The resulting positive antibody strains were further transfected into CHO-S cells stably expressing B7-H4. Blank CHO-S cells were used as control to exclude hybridoma strains of non-specific binding antibodies. Eight hybridoma strains which not only bind to recombinant proteins but also bind to antigens expressed by cells were obtained by flow sorting. Hybridoma cells at logarithmic growth phase were collected, RNAs were extracted with Trizol (Invitrogen, 15596-018) and reverse transcribed (PrimeScript™ Reverse Transcriptase, Takara #2680A). The cDNAs obtained by reverse transcription were amplified by PCR amplification using mouse Ig-Primer Set (Novagen, TB326 Rev. B 0503) and sequenced, and finally sequences of 8 murine antibodies were obtained.

The heavy and light chain variable region sequences of murine mAb 2F7 are as follows:

2F7 HCVR
SEQ ID NO: 1
EVQLVESGGGLVQPGGSLKLSCAASGFTFSNYYMSWVRQTPEKRLEWVAY
VSSGGGSTYYSDSVKGRFTISRDNAKNTLYLQMSSLKPEDTAMYYCTRES
YSQGNYFDYWGQGTTLTVSS

2F7 LCVR
SEQ ID NO: 2
DIVMTQSPATLSVTPGDRVSLSCRASQSISDYLHWYQQKSHESPRLLIKF
ASQSISGIPSRFSGSGSGSDFTLSINSVEPEDVGVYYCQNGHSFSLTFGA
GTKLELK

It contains the following CDR sequences:

| Name  | sequence        | SEQ ID NO:     |
|-------|-----------------|----------------|
| HCDR1 | GFTFSNYYMS      | SEQ ID NO: 3   |
| HCDR2 | YVSSGGGSTYYSDSVKG | SEQ ID NO: 4 |
| HCDR3 | ESYSQGNYFDY     | SEQ ID NO: 5   |
| LCDR1 | RASQSISDYLH     | SEQ ID NO: 6   |
| LCDR2 | FASQSIS         | SEQ ID NO: 7   |
| LCDR3 | QNGHSFSLT       | SEQ ID NO: 8   |

The heavy and light chain variable region sequences of M1 are as follows:

M1 HCVR
SEQ ID NO: 9
EIQLQQSGPELVMPGASVKVSCTASGYPFTTYNMYWVKQSHGKSLEWIA
YIDPYNGGTSYNQKFKGKATLTVDKSSSTAYMHLNSLTSEDSAVYYCAR
SGFYDGYYAWYFDVWGAGTTVTVSS

M1 LCVR
SEQ ID NO: 10
DVVMTQTPLSLPVSLGDQASISCRSSQSLVHSGGNTYLHWYLQKPGQSP
KLLIYKVSNRFSGVPDRFSGSGSGTDFTLKISRVEAEDLGVYFCSQSTH
VPLTFGAGTKLELK

It contains the following CDR sequences:

| Name  | sequence         | SEQ ID NO:    |
|-------|------------------|---------------|
| HCDR1 | GYPFTTYNMY       | SEQ ID NO: 11 |
| HCDR2 | YIDPYNGGTSYNQKFKG | SEQ ID NO: 12 |
| HCDR3 | SGFYDGYYAWYFDV   | SEQ ID NO: 13 |
| LCDR1 | RSSQSLVHSGGNTYLH | SEQ ID NO: 14 |
| LCDR2 | KVSNRFS          | SEQ ID NO: 15 |
| LCDR3 | SQSTHVPLT        | SEQ ID NO: 16 |

The heavy and light chain variable region sequences of murine mAb 2F8 are as follows:

2F8 HCVR
SEQ ID NO: 17
QVQLQQPGSVLVRPGASVKLSCKASGYTFTNSWMNWAKLRPGQGLEWIGG
IYPNSGNIEYNEKFKGKATLTVDTSSSTAYMDLTSLTSEDSAVYYCARDS
RFSYWGQGTLVTVSA

2F8 LCVR
SEQ ID NO: 18
DIVMTQSHKFMSTSVGDRVSITCKASQDVRTAVAWYQQKPGQSPKLLISS
TSYRYTGVPDRFTGSGSGTDFTFIISSVQAEDLAVYYCQQHYSTPLTFGA
GTKLELK

It contains the following CDR sequences:

| Name  | sequence          | SEQ ID NO:    |
|-------|-------------------|---------------|
| HCDR1 | GYTFTNSWMN        | SEQ ID NO: 19 |
| HCDR2 | GIYPNSGNIEYNEKFKG | SEQ ID NO: 20 |
| HCDR3 | DSRFSY            | SEQ ID NO: 21 |
| LCDR1 | KASQDVRTAVA       | SEQ ID NO: 22 |
| LCDR2 | STSYRYT           | SEQ ID NO: 23 |
| LCDR3 | QQHYSTPLT         | SEQ ID NO: 24 |

The heavy and light chain variable region sequences of murine mAb 2F4 are as follows:

2F4 HCVR
SEQ ID NO: 25
EVQLVESGGGLVKPGGSLKLSCAASGLTFSRYAMSWVRQTPEKRLEWVA
GISSGGSYTYYSDTVKGRFTISRDNVRNTLYLQMSSLRSEDTAMYYCGR
EYGRDYWGQGTSVTVSS

2F4 LCVR
SEQ ID NO: 26
DILMTQSPSSMSVSLGDTVSITCHASQGINSNIGWLQQKPGKSPKGLIY
HGTNLEDGVPSRFSGSGSGTDYSLTISSLESEDFADYYCVQYAQFPRTF
GGGTTLEIK

It contains the following CDR sequences:

| Name  | sequence         | SEQ ID NO:    |
|-------|------------------|---------------|
| HCDR1 | GLTFSRYAMS       | SEQ ID NO: 27 |
| HCDR2 | GISSGGSYTYYSDTVKG | SEQ ID NO: 28 |
| HCDR3 | EYGRDY           | SEQ ID NO: 29 |
| LCDR1 | HASQGINSNIG      | SEQ ID NO: 30 |
| LCDR2 | HGTNLED          | SEQ ID NO: 31 |
| LCDR3 | VQYAQFPRT        | SEQ ID NO: 32 |

The heavy and light chain variable region sequences of murine mAb 2A10 are as follows:

2A10 HCVR
SEQ ID NO: 33
EVQLVESGGGFVKPGGSLKLSCAASGFTFSTFGMSWVRQTPDKRLEWVAG

ISPGGSYTYYPDTVKGRFTISRDNARNTLYLQMSSLRSEDSAMYYCTRGR

SVWGTGTTVTVSS

2A10 LCVR
SEQ ID NO: 34
DILMTQSPSSMSVSLGDTVSITCHASQDISSNIGWLQQKPGKSFKGLIYH

GTTLEDGIPSRFSGSGSGADYSLTISSLESEDFADYYCVQSAQFPWTFGG

GTKLEIK

It contains the following CDR sequences:

| Name  | sequence         | SEQ ID NO:    |
|-------|------------------|---------------|
| HCDR1 | GFTFSTFGMS       | SEQ ID NO: 35 |
| HCDR2 | GISPGGSYTYYPDTVKG | SEQ ID NO: 36 |
| HCDR3 | GRSV             | SEQ ID NO: 37 |
| LCDR1 | HASQDISSNIG      | SEQ ID NO: 38 |
| LCDR2 | HGTTLED          | SEQ ID NO: 39 |
| LCDR3 | VQSAQFPWT        | SEQ ID NO: 40 |

The heavy and light chain variable region sequences of murine mAb 2E4 are as follows:

2E4 HCVR
SEQ ID NO: 41
QVQLQQPGSVLVRPGTSVKLSCKASGYTFTSSWMNWVKQRPGQGLEWIGG

IYPNRGTTEYNEKFKGKATLTVDTSSSTAFMDLNRLTSEDSAVYYCARDS

RFADWGQGTLVTVSA

2E4 LCVR
SEQ ID NO: 42
DIMLTQSHKFMSTSVGDRVSITCKASQDVSAAVAWYQQKPGQSPKLLISS

ASYRYTGVPDRFTGSGSGTDFTFTISSVQAEDLAVYYCQQHYNTPLTFGA

GTKLELK

It contains the following CDR sequences:

| Name  | sequence         | SEQ ID NO:    |
|-------|------------------|---------------|
| HCDR1 | GYTFTSSWMN       | SEQ ID NO: 43 |
| HCDR2 | GIYPNRGTTEYNEKFKG | SEQ ID NO: 44 |
| HCDR3 | DSRFAD           | SEQ ID NO: 45 |
| LCDR1 | KASQDVSAAVA      | SEQ ID NO: 46 |
| LCDR2 | SASYRYT          | SEQ ID NO: 47 |
| LCDR3 | QQHYNTPLT        | SEQ ID NO: 48 |

The heavy and light chain variable region sequences of murine mAb 1E4 are as follows:

1E4 HCVR
SEQ ID NO: 49
EVQLVESGGGLVKPGGSLKLSCAASGFTFSRYAMSWVRQTPEKRLEWVAG

ISSGGSYTYYPDTLKGRFTVSRDNARNTLYLQMSSLRSEDTAKYFCASQG

SNHYFDYWGQGTTLTVSS

1E4 LCVR
SEQ ID NO: 50
DTLMTQSPSSMSVSLGDTVSITCHASQGIHNNIGWLQQKPGKSFKALIYH

GTNLEDGVPSRFSGSGSGADYSLIISSLESEDFADYYCVQYAQFPYTFGG

GTKLEIK

It contains the following CDR sequences:

| Name  | sequence         | SEQ ID NO:    |
|-------|------------------|---------------|
| HCDR1 | GFTFSRYAMS       | SEQ ID NO: 51 |
| HCDR2 | GISSGGSYTYYPDTLKG | SEQ ID NO: 52 |
| HCDR3 | QGSNHYFDY        | SEQ ID NO: 53 |
| LCDR1 | HASQGIHNNIG      | SEQ ID NO: 54 |
| LCDR2 | HGTNLED          | SEQ ID NO: 55 |
| LCDR3 | VQYAQFPYT        | SEQ ID NO: 56 |

The heavy and light chain variable region sequences of murine mAb 2G6 are as follows:

2G6 HCVR
SEQ ID NO: 57
EVQLVESGGGLVKPGGSLKLSCAASGFTFSRYGMSWVRQTPEKRLEWVAG

INGGGSYTYYLDTVKGRFTISRDNSRNTLYLQMSSLRSEDTAMYYCVSQG

SNYYFDYWGQGTTLTVSS

2G6 LCVR
SEQ ID NO: 58
DIRMTQSPSSMSVSLGDTVSITCHASQGISSNIGWLQQKPGKSFKALIYH

GTNLEDGVPSRFSGSGSGADYSLTISSLESEDFADYYCVQYAQFPYTFGG

GTKLEIK

It contains the following CDR sequences:

| Name  | sequence         | SEQ ID NO:    |
|-------|------------------|---------------|
| HCDR1 | GFTFSRYGMS       | SEQ ID NO: 59 |
| HCDR2 | GINGGGSYTYYLDTVKG | SEQ ID NO: 60 |
| HCDR3 | QGSNYYFDY        | SEQ ID NO: 61 |
| LCDR1 | HASQGISSNIG      | SEQ ID NO: 62 |
| LCDR2 | HGTNLED          | SEQ ID NO: 63 |
| LCDR3 | VQYAQFPYT        | SEQ ID NO: 64 |

The heavy and light chain variable region sequences of murine mAb 1C9 are as follows:

1C9 HCVR
SEQ ID NO: 65
QVQLQQPGSVLVRPGASVKLSCKASGDTFTTYWMNWVKQRPGQGLEWIGG

IYLNSGSSEYNEKFKGKATLSVDTSSSTAYMDLSSLTSEDSAVYYCARDS

RFSYWGQGTLVTVSA

1C9 LCVR
SEQ ID NO: 66
DIVMTQSHKFLSTSVGDRVSITCKASQDVSTAVAWYQQKPGQSPELLISS

ASYRYTGVPDRFTGSGSGTDFTFTISSVQAEDLAVYYCQQHYNTPLTFGA

GTQLELK

It contains the following CDR sequences:

| Name | sequence | SEQ ID NO: |
|---|---|---|
| HCDR1 | GDTFTTY | SEQ ID NO: 67 |
| HCDR2 | YLNSGS | SEQ ID NO: 68 |
| HCDR3 | DSRFSY | SEQ ID NO: 69 |
| LCDR1 | KASQDVSTAVA | SEQ ID NO: 70 |
| LCDR2 | SASYRYT | SEQ ID NO: 71 |
| LCDR3 | QQHYNTPLT | SEQ ID NO: 72 |

The heavy and light chain variable regions of each mouse mAb were cloned into the human IgG1 heavy chain constant region and the kappa light chain constant region respectively, and then were purified, identified, and tested for activity as described in Example 4.

Example 3: Detection of In Vitro Binding Activity of the Antibodies (1) In Vitro Indirect ELISA Binding Assay:

HuB7-H4 His protein (Sino Biological Inc., cat #10738-H08H) was diluted to a concentration of 1 μg/ml with PBS, pH 7.4, added into a 96-well high-affinity microtiter plate at a volume of 100 μl/well, and incubated at 4° C. overnight (16-20 hours). The plate was washed with PBST (PBS comprising 0.05% Tween-20, pH 7.4) four times, and then 150 μl/well of 3% bovine serum albumin (BSA) blocking solution diluted in PBST was added, and incubated at room temperature for 1 hour for blocking. After the blocking was finished, the blocking solution was discarded and the plate was washed 4 times with PBST buffer.

The antibodies to be tested were diluted with PBST comprising 3% BSA at a gradient of 10-fold dilution, starting from 1 μM with a total of 10 doses. The dilutions were added into the plate at 100 μl/well, and incubated at room temperature for 1 hour. After the incubation was finished, the plate was washed 4 times with PBST, 100 μl/well of HRP-labeled goat anti-human secondary antibody (Abeam, cat #ab97225) diluted in PBST comprising 3% BSA was added and incubated at room temperature for 1 hour. The plate was washed 4 times with PBST, 100 μl/well TMB chromogenic substrate (Cell Signaling Technology, cat #7004S) was added and incubated at room temperature in darkness for 1 minute, and 100 μl/well of Stop Solution (Cell Signaling Technology, cat #7002S) was added to terminate the reaction. The absorbance was read at 450 nm using a microplate reader (BioTek, model Synergy H1), and the data was analyzed. The curve of concentration vs. signal value was plotted and the results were analyzed, as shown in the following table:

| Chimeric antibody | $EC_{50}$ for the binding to human B7-H4 His antigen (nM) |
|---|---|
| M1 | 0.063 |
| 2A10 | 0.071 |
| 2F4 | 0.056 |
| 2F7 | 0.17 |
| 2F8 | 0.067 |
| 2G6 | 0.081 |
| 1C9 | 0.068 |

(2) Competitive ELISA Assay:

HuB7-H4 His protein (Sino Biological Inc., cat #10738-H08H) was diluted to a concentration of 1 μg/ml with PBS, pH 7.4, added into a 96-well high-affinity microtiter plate at a volume of 100 μl/well, and incubated at 4° C. overnight (16-20 hours). The plate was washed 4 times with PBST (PBS comprising 0.05% Tween-20, pH 7.4), 150 μl/well of 3% bovine serum albumin (BSA) blocking solution diluted in PBST was added, and incubated at room temperature for 1 hour. After the blocking was finished, the blocking solution was discarded and the plate was washed 4 times with PBST buffer.

0.1 nM reference chimeric antibody was prepared with PBST comprising 3% BSA, and was used as dilution solution to dilute the murine antibodies to be tested, obtain a gradient of 10-fold dilution, starting from 100 nM with a total of 10 doses. The diluted antibodies were added into the plate at 100 μl/well, and incubated for 1 hour at room temperature. After the incubation was finished, the plate was washed 4 times with PBST, and 100 μl/well of HRP-labeled goat anti-human secondary antibody (Abcam, cat #ab97225) diluted in PBST comprising 3% BSA was added, and incubated for 1 hour at room temperature. The plate was washed 4 times with PBST, and then 100 μl/well TMB chromogenic substrate (Cell Signaling Technology, cat #7004S) was added, and incubated at room temperature for 1 minute in darkness. 100 μl/well of Stop Solution (Cell Signaling Technology, cat #7002S) was added to terminate the reaction, and the absorbance was read at 450 nm using a microplate reader (BioTek, model Synergy H1). The data was analyzed. Competitive inhibition rate=((reference antibody absorbance−competitive antibody absorbance)/Abv antibody absorbance)*100.

(3) In Vitro Capture ELISA Binding Assay:

The goat anti-mouse IgG secondary antibody (Jackson Immuno Research, cat #115-006-071) was diluted to a concentration of 2 μg/ml with PBS buffer, pH 7.4, added into a 96-well microtiter plate at a volume of 100 μl/well, and incubated in an incubator at 37° C. for 2 hours. The plate was washed once with PBST, 5% skim milk (Bright Dairy, Skim Milk Powder) blocking solution diluted in PBST was added at 200 μl/well, and incubated at 37° C. for 2 hours or at 4° C. overnight (16-18 hours) for blocking. After the blocking was finished, the blocking solution was discarded and the plate was washed 4 times with PBST.

The mouse sera or purified recombinant antibodies to be tested were diluted to various concentrations with sample dilution comprising 5% NHS (PBST with 2.5% skim milk), incubated for 40 minutes at room temperature, added into a plate at 100 μl/well, and incubated in an incubator for 40 minutes at 37° C. After the incubation was finished, the plate was washed 4 times with PBST, 100 μl/well of biotinylated huB7-H4-his (Sino Biological #10738-H08H) protein solution diluted in sample dilution solution was added, and incubated at 37° C. for 40 minutes. After the incubation was finished, the plate was washed 4 times with PBST, 100 μl/well of HRP-labeled streptavidin (Jackson Immuno Research, cat #016-030-084) diluted in PBST was added, and incubated at 37° C. for 40 minutes. After the plate was washed 4 times with PBST, 100 μl/well TMB chromogenic substrate (InnoReagents Biotechnology Co., Ltd.) was added, incubated at room temperature for 10-15 min in darkness, 50 μl/well 1M $H_2SO_4$ was added to stop the reaction. The absorbance was read at 450 nm using a microplate reader (Beijing Perlong New Technology Co., Ltd., model DNM-9602) and data was analyzed.

(4) In Vitro Cell Binding Assay:

The cultured SK-BR3 cells or cells stably transfected with CHO-huB7-H4 were collected, and then plated onto a 96-well U-bottom plate at cell density of $1 \times 10^5$ $2 \times 10^5$ cells per well. The supernatant was removed by centrifuging at 1200 g for 5 min, 100 μl of serially diluted antibody solutions or mouse immune sera were added, and incubated at 4° C. for 60 min, and the supernatant was removed by centrifuging at 1200 g for 5 min. The cells were washed twice with PBS, fluorescent labeled secondary antibody (PE-GAM or PE-GAH) was added at 100 μl per well, incubated for 60 min at 4° C., and centrifuged at 1200 g for 5 min to remove the supernatant. The cells were washed twice with PBS, and then were re-suspended in PBS. The signals were detected using flow cytometer, and the concentration curve was plotted and results were analyzed.

Example 4: Construction and Expression of Anti-B7-H4 Recombinant Chimeric Antibodies Site-directed amino acid mutations were made in the FR region(s) (framework regions) of the heavy chain variable region (VH) and the light chain variable region (VL) for each murine antibody of the present invention. Different humanized antibody heavy and light chain were designed according to different combinations of amino acid mutations. Cells transfected with plasmids of various combinations of heavy and light chains would be used to produce humanized antibodies.

The heavy chain vector was designed as follows: signal peptide+mutated heavy chain variable region sequence+human IgG1 constant region sequence.

The light chain vector was designed as follows: signal peptide+mutated light chain variable region sequence+human Kappa constant region sequence.

The above sequences were inserted into pCEP4 vector respectively. Expression vectors were synthesized according to the above design, the resulting vector plasmids were extracted with maxi extraction kit, and were validated by sequencing. The validated plasmids were transfected into human 293F cells with PEI and cultured continuously. The 293F cells were cultured in serum-free medium (Shanghai opmbiosciences, OPM-293CD03) to logarithmic growth phase for cell transfection. 21.4 μg of the humanized antibody light chain plasmid and 23.6 μg of the humanized antibody heavy chain plasmid were dissolved in 10 ml of Opti-MEM® I Reduced Serum Medium (GIBCO, 31985-070), mixed well, added 200 μg of PEI, mixed well, incubated for 15 min at RT, and added into 50 mL of cells. Cell culture conditions were as follows: 5% $CO_2$, 37° C., 125 rpm/min. During the culture period, medium was replenished on day 1 and day 3, until the cell viability reached to less than 70%. The cell supernatant was collected and centrifuged for filtration. After centrifugation, the cell culture was applied to an affinity column for antibody purification. The purified chimeric antibodies were finally obtained after the column was washed with phosphate buffer, eluted with glycine hydrochloride buffer (0.1 M Gly-HCl, pH 2.7), neutralized with 1 M Tris hydrochloric acid pH 9.0, and dialyzed with phosphate buffer.

Example 5: In Vitro Binding Affinity and Kinetic Assay

Biacore method is recognized as a method for the objective detection of the affinity and kinetics between proteins. The affinities and binding kinetics of the B7-H4 antibodies of the invention to be tested were analyzed by Biacore T200 (GE).

The anti-B7-H4 antibody of the present invention to be tested was covalently linked to CM5 (GE) chip by NHS standard amino coupling method using a kit provided by Biacore. Then, a). 50 nM human huB7-H4-his protein (Sino Biological #10738-H08H) diluted by the same buffer was loaded at a flow rate of 10 μL/min, and the chip was regenerated with the regeneration reagent provided in the kit. Antigen-antibody binding kinetics were recorded for 3 minutes and dissociation kinetics were recorded for 10 minutes. The resulting data were analyzed by GE's BIAevaluation Software using 1:1 (Langmuir) binding model. The kd (koff) data of each murine antibody estimated by this method were shown in the following table.

| Murine antibody | antigen | dissociation rate kd (1/s) |
|---|---|---|
| 2F7 | huB7-H4-his | 2.53E−03 |
| 2F8 | | 6.87E−05 |
| M1 | | 3.98E−05 |
| 2A10 | | 3.31E−04 |
| 2G6 | | 8.91E−05 |
| 2F4 | | 1.66E−03 |
| 2E4 | | 5.97E−05 |
| 1E4 | | 2.93E−04 | b). A series of concentrations of human huB7-H4-his protein diluted by the same buffer were respectively loaded at the flow rate of 10 μL/min and the chip was regenerated with the regeneration reagent provided in the kit. Antigen-antibody binding kinetics were recorded for 3 minutes and dissociation kinetics were recorded for 10 minutes. The resulting data were analyzed by GE's BIAevaluation Software using 1:1 (Langmuir) binding model. The ka(kon), kd (koff) and $K_D$ value for each chimeric antibody estimated by this method were shown in the following table.

| chimeric antibody | antigen | Association rate $k_a$ (1/M*s) | dissociation rate $k_d$ (1/s) | affinity $K_D$ |
|---|---|---|---|---|
| ch-2F7 | huB7-H4-his | 4.417E+04 | 3.038E−03 | 68.8 nM |
| ch-2F8 | | 1.126E+06 | 1.136E−04 | 119 pM |
| ch-M1 | | 6.743E+05 | 9.411E−05 | 140 pM |
| ch-2F4 | | 1.040E+06 | 2.593E−03 | 2.5 nM |

Example 6: Humanization of Mouse Antibodies

Humanization of murine anti-human B7-H4 monoclonal antibodies was performed as disclosed in many literatures in the art. Briefly, the parental (murine antibody) constant domain was replaced with human constant domain, and the human antibody sequences were selected on the basis of the homology between the murine antibody and the human antibody. In the present invention, the murine candidate molecules 2F7, 2F8, 2G6 and 1C9 were subjected to humanization.

Based on the typical structure of the resulting murine antibody VH/VL CDR, the heavy and light chain variable region sequences were compared with the human antibody germline database to obtain human germline template with high homology.

The CDR regions of the murine antibodies 2F7, 2F8, 2G6 and 1C9 were grafted onto the selected corresponding humanized template. For 2F8, the HCDR1 region (GYTFTNSWMN, SEQ ID NO: 19) and HCDR2 region (GIYPNSGNIEYNEKFKG, SEQ ID NO: 20) were mutated to GYTFTSSWMN (SEQ ID NO: 73) and GIYPNRGNIEYNEKFKG (SEQ ID NO: 74), respectively, to remove potential unstable de-acetylation sites. The humanized variable regions were replaced and recombined with IgG constant region (preferably IgG1 for the heavy chain and x for the light chain). Then, based on the three-dimensional structure of the murine antibody, back mutations were made on the embedded residues, residues which directly interacted with the CDRs and the residues which have an important impact on the conformation of VL and VH. The chemically instable amino acid residues in CDR regions were optimized. The antibodies resulting from the combination of humanized light and heavy chain variable region sequences were obtained and detected.

The humanized hu2F7, hu2F8, hu2G6 and hu1C9 antibody molecules were finally selected by expression test and comparison of the number of back mutations, and the respective heavy and light chain variable region sequences were shown in SEQ ID NOs: 75-82, and the respective heavy and light chain sequences were shown in SEQ ID NOs: 83-90.

hu2F7 HCVR
SEQ ID NO: 75
EVQLVESGGGLVQPGGSLRLSCAASGFTFSNYYMSWVRQAPGKGLEWVAY

VSSGGGSTYYSDSVKGRFTISRDNAKNTLYLQMSSLRAEDTAVYYCTRES

YSQGNYFDYWGQGTTVTVSS

SEQ ID NO: 91
EVQLVESGGGLVQPGGSLRLSCAASGFTFSNYYMSWVRQAPGKGLEWVAY

VSSGGGSTYYSDSVKGRFTISRDNAKNTLYLQMSSLRAEDTAVYYCARES

YSQGNYFDYWGQGTTVTVSS hu2F7 LCVR
SEQ ID NO: 76
EIVMTQSPATLSLSPGERATLSCRASQSISDYLHWYQQKPGQSPRLLIKF

ASQSISGIPARFSGSGSGTDFTLTISSLEPEDFAVYYCQNGHSFSLTFGQ

GTKLEIK

SEQ ID NO: 92
EIVLTQSPATLSLSPGERATLSCRASQSISDYLHWYQQKPGQAPRLLIYF

ASQSISGIPARFSGSGSGTDFTLTISSLEPEDFAVYYCQNGHSFSLTFGQ

GTKLEIK

SEQ ID NO: 93
EIVLTQSPATLSLSPGERATLSCRASQSISDYLHWYQQKPGQAPRLLIKF

ASQSISGIPARFSGSGSGTDFTLTISSLEPEDFAVYYCQNGHSFSLTFGQ

GTKLEIK

SEQ ID NO: 94
EIVMTQSPATLSLSPGERATLSCRASQSISDYLHWYQQKPGQAPRLLIKF

ASQSISGIPARFSGSGSGTDFTLTISSLEPEDFAVYYCQNGHSFSLTFGQ

GTKLEIK hu2F8 HCVR
SEQ ID NO: 77
EVQLVQSGAEVKKPGASVKVSCKASGYTFTSSWMNWVRQAPGQRLEWMGG

IYPNRGNIEYNEKFKGRVTLTVDTSASTAYMELSSLRSEDTAVYYCARDS

RFSYWGQGTLVTVSS

SEQ ID NO: 95
EVQLVQSGAEVKKPGASVKVSCKASGYTFTSSWMNWVRQAPGQRLEWMGG

IYPNRGNIEYNEKFKGRVTITVDTSASTAYMELSSLRSEDTAVYYCARDS

RFSYWGQGTLVTVSS

SEQ ID NO: 96
EVQLVQSGAEVKKPGASVKVSCKASGYTFTSSWMNWVRQAPGQGLEWMGG

IYPNRGNIEYNEKFKGRVTLTVDTSASTAYMELSSLRSEDTAVYYCARDS

RFSYWGQGTLVTVSS hu2F8 LCVR
SEQ ID NO: 78
DIQMTQSPSSLSASVGDRVTITCKASQDVRTAVAWYQQKPGKAPKLLISS

TSYRYTGVPSRFSGSGSGTDFTFTISSLQPEDIATYYCQQHYSTPLTFGG

GTKVEIK

SEQ ID NO: 97
DIVMTQSPSSLSASVGDRVTITCKASQDVRTAVAWYQQKPGKAPKLLISS

TSYRYTGVPSRFSGSGSGTDFTFTISSLQPEDIATYYCQQHYSTPLTFGG

GTKVEIK

SEQ ID NO: 98
DIVMTQSPSSLSASVGDRVTITCKASQDVRTAVAWYQQKPGKSPKLLISS

TSYRYTGVPSRFSGSGSGTDFTFTISSLQPEDIATYYCQQHYSTPLTFGG

GTKVEIK hu2G6 HCVR
SEQ ID NO: 79
EVQLLESGGGLVQPGGSLRLSCAASGFTFSRYGMSWVRQAPGKGLEWVSG

INGGGSYTYYLDTVKGRFTISRDNARNTLYLQMSSLRAEDTAVYYCVSQG

SNYYFDYWGQGTLVTVSS hu2G6 LCVR
SEQ ID NO: 80
DIRMTQSPSSLSASVGDRVTITCHASQGISSNIGWLQQKPGKAPKALIYH

GTNLEDGVPSRFSGSGSGADYTLTISSLQPEDFATYYCVQYAQFPYTFGG

GTKVEIK hu1C9 HCVR

SEQ ID NO: 81
EVQLVQSGAEVKKPGASVKVSCKASGDTFTTYWMNWVRQAPGQRLEWMGG
IYLNRGSSEYNEKFKGRVTLTVDTSASTAYMELSSLRSEDTAVYYCARDS
RFSYWGQGTLVTVSS hu1C9 LCVR

SEQ ID NO: 82
DIQMTQSPSSLSASVGDRVTITCKASQDVSTAVAWYQQKPGKAPKLLISS
ASYRYTGVPSRFSGSGSGTDFTFTISSLQPEDIATYYCQQHYNTPLTFGG
GTKVEIK hu2F7 HC

SEQ ID NO: 83
EVQLVESGGGLVQPGGSLRLSCAASGFTFSNYYMSWVRQAPGKGLEWVAY
VSSGGGSTYYSDSVKGRFTISRDNAKNTLYLQMSSLRAEDTAVYYCTRES
YSQGNYFDYWGQGTTVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK hu2F7 LC

SEQ ID NO: 84
EIVMTQSPATLSLSPGERATLSCRASQSISDYLHWYQQKPGQSPRLLIKF
ASQSISGIPARFSGSGSGTDFTLTISSLEPEDFAVYYCQNGHSFSLTFGQ
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC hu2F8 HC

SEQ ID NO: 85
EVQLVQSGAEVKKPGASVKVSCKASGYTFTSSWMNWVRQAPGQRLEWMGG
IYPNRGNIEYNEKFKGRVTLTVDTSASTAYMELSSLRSEDTAVYYCARDS
RFSYWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDG
SFFLYSKLTVDKSRWQQGNVFSCSVMHEALHNHYTQKSLSLSPGK hu2F8 LC

SEQ ID NO: 86
DIQMTQSPSSLSASVGDRVTITCKASQDVRTAVAWYQQKPGKAPKLLISS
TSYRYTGVPSRFSGSGSGTDFTFTISSLQPEDIATYYCQQHYSTPLTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC hu2G6 HC

SEQ ID NO: 87
EVQLLESGGGLVQPGGSLRLSCAASGFTFSRYGMSWVRQAPGKGLEWVSG
INGGGSYTYYLDTVKGRFTISRDNARNTLYLQMSSLRAEDTAVYYCVSQG
SNYYFDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGK hu2G6 LC

SEQ ID NO: 88
DIRMTQSPSSLSASVGDRVTITCHASQGISSNIGWLQQKPGKAPKALIYH
GTNLEDGVPSRFSGSGSGADYTLTISSLQPEDFATYYCVQYAQFPYTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC hu1C9 HC

SEQ ID NO: 89
EVQLVQSGAEVKKPGASVKVSCKASGDTFTTYWMNWVRQAPGQRLEWMGG
IYLNRGSSEYNEKFKGRVTLTVDTSASTAYMELSSLRSEDTAVYYCARDS
RFSYWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDG
SFFLYSKLTVDKSRWQQGNVFSCSVMHEALHNHYTQKSLSLSPGK hu1C9 LC

SEQ ID NO: 90
DIQMTQSPSSLSASVGDRVTITCKASQDVSTAVAWYQQKPGKAPKLLISS
ASYRYTGVPSRFSGSGSGTDFTFTISSLQPEDIATYYCQQHYNTPLTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC cDNA fragments were synthesized based on the amino acid sequences of the above humanized antibody light and heavy chains, and inserted into pcDNA3.1 expression vectors (Life Technologies Cat. No. V790-20). The expression vectors and the transfection reagent PEI (Polysciences, Inc. Cat. No. 23966) were transfected into HEK293 cells (Life Technologies Cat. No. 11625019) at a ratio of 1:2 and incubated in a $CO_2$ incubator for 4-5 day. The expressed antibodies were recovered by centrifugation, and antibody purification was carried out in accordance with the method of Example 4 to obtain humanized antibody proteins hu2F7 and hu2F8 of the present invention.

Example 7: Determination of Activity of Humanized Antibodies

The following in vitro assays were performed on humanized antibodies hu2F7 and hu2F8:

1. In Vitro Cell Binding Assay:

The cultured MX-1 cells were collected, cell density was adjusted with PBS pH 7.4, then plated onto a 96-well V-shaped bottom plate with $1\times10^5$ cells per well, and centrifuged at 2000 rpm for 5 minutes to remove supernatant. 100 μl of the serially diluted chimeric antibody solution was added (diluted with 0.5% BSA in PBS to obtain a gradient of 3-fold dilutions, starting from 1 μM, with a total of 10 doses) into each well, mixed, and incubated for 1 hour at 4° C. with shaking; the culture was centrifuged at 2000 rpm for 5 minutes to remove the supernatant, and the cells were washed twice with PBS, and 100 μl of FITC-labeled goat anti-human secondary antibody (Abeam, cat #ab97224) diluted with 0.5% BSA in PBS was added into each well, mixed well and incubated for 30 minutes at 4° C. in a shaker. Centrifugation was performed at 2000 rpm for 5 minutes and the supernatant was removed. Cells were washed twice with PBS and resuspended in PBS. The signals were detected using flow cytometer (BECKMANCOULTER, model DxFLEX), and the concentration curve was plotted and the results were analyzed. As indicated in the table and figure, humanized antibodies 2F7, 2F8, 2G6 and 1C9 show positive bindings to MX-1 cells on which B7-H4 was highly expressed.

| Name of antibody | FACS Binding $EC_{50}$ (nM) for MX-1 cell |
|---|---|
| hu2F7 | 7.32 |
| hu2F8 | 7.26 |
| hu2G6 | 14.3 |
| hu1C9 | 7.25 |

2. Affinity kinetic assay (method procedures were the same as those described in Example 5). The results were shown in the table below. The humanized antibodies hu2F7, hu2F8, hu2G6 and hu1C9 all show strong affinity for the human B7-H4 antigen protein.

| antibody | antigen | Association rate $k_a$ (1/M*s) | Dissociation rate $k_d$ (1/s) | affinity $K_D$ |
|---|---|---|---|---|
| hu2F7 | hu-B7-H4-his | 3.29e+05 | 2.49e−04 | 7.57e−10 |
| hu2F8 | | 4.47e+05 | 1.12e−04 | 2.50e−10 |
| hu2G6 | | 7.41e+05 | 1.00e−05 | 1.35e−11 |
| hu1C9 | | 3.35e+05 | 1.00e−05 | 2.98e−11 |

Figure 2:
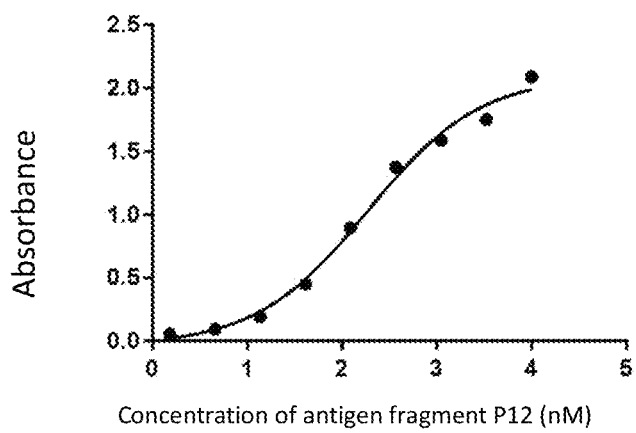
FIG. 2: Indirect ELISA binding assays, showing the antigenic epitope to which the anti-B7-H4 antibody hu2F7 binds.

Example 8: Determination of Binding Epitopes Recognized by the Humanized Antibodies The method procedures were the same as described in Example 3 (1): in vitro indirect ELISA binding assay. The B7-H4 of SEQ ID NO: 100 was degraded into antigen fragments of 20 amino acids in length, and the antigen fragment P12 (amino acid sequence: TVASAGNIGEDGILSCTFEP) was found to be specifically bound by the humanized anti-B7-H4 antibody hu2F7, in in vitro indirect ELISA binding assay. The results were shown in FIG. 2. To further confirm the epitope to which the antibody binds, alanine scan was performed on the antigen fragment P12, that is, each single amino acid located in P12 was mutated to alanine respectively. It was found in in vitro indirect ELISA binding assay that mutations in amino acid sequence ILSCTFE portion significantly attenuated binding of the antibody to the antigen fragment, showing that the antibody binding epitope was located in the amino acid sequence portion of ILSCTFE (SEQ ID NO: 109) comprised in the amino acid sequence TVASAGNIGEDGILSCTFEP. The results were shown in the following table:

| Antigen fragment sequence | SEQ ID NO: | Affinity EC50 (nM) |
|---|---|---|
| TVASAGNIGEDGILSCTFEP | 101 | 117.9 |
| TVASAGNIGEDGALSCTFEP | 102 | 770.6 |
| TVASAGNIGEDGIASCTFEP | 103 | 1476 |
| TVASAGNIGEDGILSATFEP | 104 | 2006 |
| TVASAGNIGEDGILSCAFEP | 105 | 462.8 |
| TVASAGNIGEDGILSCTAEP | 106 | 986.5 |
| TVASAGNIGEDGILSCTFAP | 107 | 662.5 |

It was found in in vitro indirect ELISA binding assay that the antigen fragment P12 (amino acid sequence: TVASAGNIGEDGILSCTFEP) was specifically bound by the humanized anti-B7-H4 antibody, hu1C9. The results were shown in the table below. To further confirm the epitope to which the antibody binds, alanine scan was performed on the antigen fragment P12, that is, each single amino acid located in P12 was mutated to alanine respectively. It was found in in vitro indirect ELISA binding assay that mutations in amino acid sequence LSCTF portion significantly attenuated binding of the antibody to the antigen fragment, showing that the antibody binding epitope was located in the amino acid sequence portion of LSCTF (SEQ ID NO: 110) comprised in the amino acid sequence TVASAGNIGEDGILSCTFEP. The results were shown in the following table:

| Antigen fragment sequence | SEQ ID NO: | Affinity EC50 (nM) |
|---|---|---|
| TVASAGNIGEDGILSCTFEP | 101 | 271.7 |
| TVASAGNIGEDGIASCTFEP | 103 | 466.9 |
| TVASAGNIGEDGILSATFEP | 104 | 292.3 |
| TVASAGNIGEDGILSCTAEP | 106 | 487.9 |

It was found in in vitro indirect ELISA binding assay that the antigen fragment P12 (amino acid sequence: TVASAGNIGEDGILSCTFEP) was specifically bound by the humanized anti-B7-H4 antibody, hu2G6. The results were shown in the table below. To further confirm the epitope to which the antibody binds, alanine scan was performed on the antigen fragment P12, that is, each single amino acid located in P12 was mutated to alanine respectively. It was found in in vitro indirect ELISA binding assay that mutations in amino acid sequence ILSCTFEP portion significantly attenuated binding of the antibody to the antigen fragment, showing that the antibody binding epitope was located in the amino acid sequence portion of ILSCTFEP (SEQ ID NO: 111) comprised in the amino acid sequence TVASAGNIGEDGILSCTFEP. The results were shown in the following table:

| Antigen fragment sequence | SEQ ID NO: | Affinity EC50 (nM) |
|---|---|---|
| TVASAGNIGEDGILSCTFEP | 101 | 792.6 |
| TVASAGNIGEDGALSCTFEP | 102 | 2626 |
| TVASAGNIGEDGIASCTFEP | 103 | 3158 |
| TVASAGNIGEDGILSATFEP | 104 | 3480 |
| TVASAGNIGEDGILSCAFEP | 105 | 2289 |
| TVASAGNIGEDGILSCTAEP | 106 | 2600 |
| TVASAGNIGEDGILSCTFEA | 108 | 2372 |

Example 9: Anti-Tumor Effect of Humanized Antibodies

Figure 3:
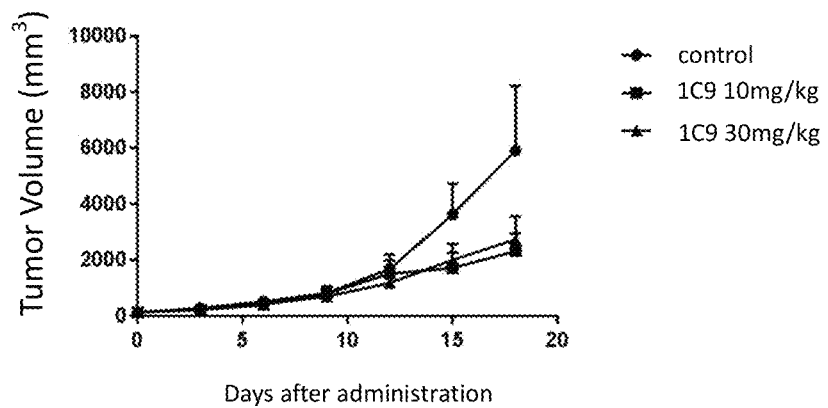
FIG. 3: Pharmacological assay in mice, showing the anti-tumor effect of anti-B7-H4 antibody hu1C9.

MC38 tumor cells were implanted into mice into which human B7-H4 gene was introduced by gene editing technology. When the tumor reached an average of 100 mm³, the mice were injected with control or humanized B7-H4 antibody hu1C9 (10 mg/kg or 30 mg/kg) every 3 days. By observing the size of the tumor, it was found that hu1C9 has a significant effect on inhibiting tumor growth and has an anti-tumor effect. The specific results were shown in FIG. 3 and the following table:

| | Volume of the tumor (mean, mm³) | | | | | | |
|---|---|---|---|---|---|---|---|
| | Day 0 | Day 3 | Day 6 | Day 9 | Day 12 | Day 15 | Day 18 |
| Blank control group | 136.2979 | 290.2921 | 526.7519 | 820.9497 | 1689.954 | 3625.686 | 5913.385 |
| 1C9 (10 mg/kg) | 146.5273 | 231.8861 | 404.833 | 794.0959 | 1519.589 | 1717.092 | 2326.687 |
| 1C9 (30 mg/kg) | 139.3148 | 256.9988 | 437.9834 | 702.0555 | 1190.775 | 2008.451 | 2744.415 |

Example 10: Effect of Humanized Antibodies on Enhancing Immunity

Figure 4:
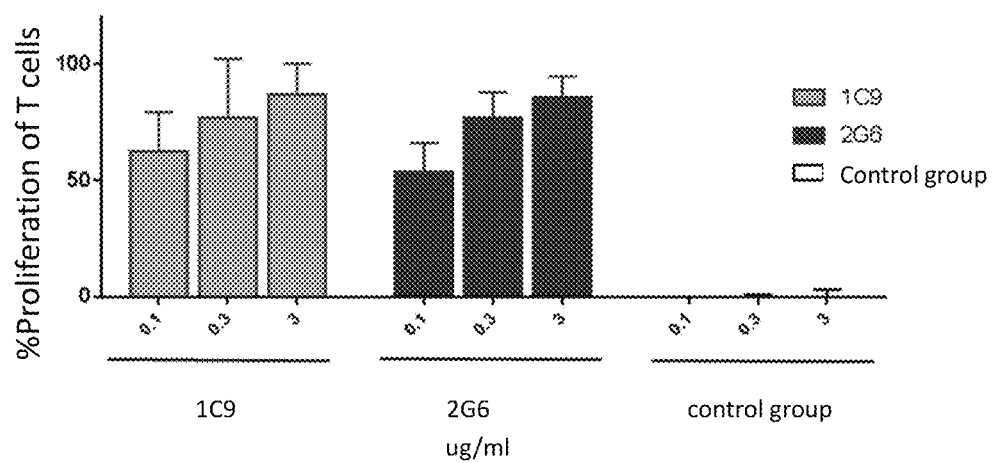
FIG. 4: Immunological function assay, showing effect of anti-B7-H4 antibodies hu1C9 and hu2G6 in enhancing immunity (T cell proliferation).

The anti-tumor effect of anti-B7-H4 may be mediated by enhancing immune effects against tumors. To validate this mechanism, CD4-positive T cells were extracted from human peripheral blood. Various concentrations of anti-B7-H4 antibodies, including the humanized antibody hu2G6 and hu1C9, were added into the cultured T cells. The specific results were shown in FIG. 4 and the table below. The humanized antibody hu2G6 and the humanized antibody hu1C9 have an effect on enhancing proliferation of T cells, and can achieve an antitumor effect by enhancing immune effects against tumors.

| | Proliferation of T cells (percentage, mean) | | |
|---|---|---|---|
| dosage | 1C9 | 2G6 | Blank control group |
| 0.1 (µg/ml) | 62.49425 | 53.6423 | −12.7833 |
| 0.3 (µg/ml) | 76.83938 | 76.88089 | −4.12145 |
| 3 (µg/ml) | 86.96902 | 85.86148 | −4.39787 |

What is claimed is:

1. An anti-B7-H4 antibody or antigen-binding fragment thereof, comprising an antibody light chain variable region and an antibody heavy chain variable region combination selected from the group consisting of:
   i) an antibody light chain variable region comprising LCDR1, LCDR2 and LCDR3 as shown in SEQ ID NO: 6, SEQ ID NO: 7 and SEQ ID NO: 8, respectively; and an antibody heavy chain variable region comprising HCDR1, HCDR2 and HCDR3 as shown in SEQ ID NO: 3, SEQ ID NO: 4 and SEQ ID NO: 5, respectively;
   ii) an antibody light chain variable region comprising LCDR1, LCDR2 and LCDR3 as shown in SEQ ID NO: 14, SEQ ID NO: 15 and SEQ ID NO: 16, respectively; and an antibody heavy chain variable region comprising HCDR1, HCDR2 and HCDR3 as shown in SEQ ID NO: 11, SEQ ID NO: 12 and SEQ ID NO: 13, respectively;
   iii) an antibody light chain variable region comprising LCDR1, LCDR2 and LCDR3 as shown in SEQ ID NO: 22, SEQ ID NO: 23 and SEQ ID NO: 24, respectively; and an antibody heavy chain variable region comprising HCDR1, HCDR2 and HCDR3 as shown in SEQ ID NO: 19, SEQ ID NO: 20 and SEQ ID NO: 21, respectively;
iv) an antibody light chain variable region comprising LCDR1, LCDR2 and LCDR3 as shown in SEQ ID NO: 30, SEQ ID NO: 31 and SEQ ID NO: 32, respectively; and an antibody heavy chain variable region comprising HCDR1, HCDR2 and HCDR3 as shown in SEQ ID NO: 27, SEQ ID NO: 28 and SEQ ID NO: 29, respectively;
v) an antibody light chain variable region comprising LCDR1, LCDR2 and LCDR3 as shown in SEQ ID NO: 38, SEQ ID NO: 39 and SEQ ID NO: 40, respectively; and an antibody heavy chain variable region comprising HCDR1, HCDR2 and HCDR3 as shown in SEQ ID NO: 35, SEQ ID NO: 36 and SEQ ID NO: 37, respectively;
vi) an antibody light chain variable region comprising LCDR1, LCDR2 and LCDR3 as shown in SEQ ID NO: 46, SEQ ID NO: 47 and SEQ ID NO: 48, respectively; and an antibody heavy chain variable region comprising HCDR1, HCDR2 and HCDR3 as shown in SEQ ID NO: 43, SEQ ID NO: 44 and SEQ ID NO: 45, respectively;
vii) an antibody light chain variable region comprising LCDR1, LCDR2 and LCDR3 as shown in SEQ ID NO: 54, SEQ ID NO: 55 and SEQ ID NO: 56, respectively; and an antibody heavy chain variable region comprising HCDR1, HCDR2 and HCDR3 as shown in SEQ ID NO: 51, SEQ ID NO: 52 and SEQ ID NO: 53, respectively;
viii) an antibody light chain variable region comprising LCDR1, LCDR2 and LCDR3 as shown in SEQ ID NO: 62, SEQ ID NO: 63 and SEQ ID NO: 64, respectively; and an antibody heavy chain variable region comprising HCDR1, HCDR2 and HCDR3 as shown in SEQ ID NO: 59, SEQ ID NO: 60 and SEQ ID NO: 61, respectively;
ix) an antibody light chain variable region comprising LCDR1, LCDR2 and LCDR3 as shown in SEQ ID NO: 70, SEQ ID NO: 71 and SEQ ID NO: 72, respectively; and an antibody heavy chain variable region comprising HCDR1, HCDR2 and HCDR3 as shown in SEQ ID NO: 67, SEQ ID NO: 68 and SEQ ID NO: 69, respectively; and
x) an antibody light chain variable region comprising LCDR1, LCDR2 and LCDR3 as shown in SEQ ID NO: 22, SEQ ID NO: 23 and SEQ ID NO: 24, respectively; and an antibody heavy chain variable region comprising HCDR1, HCDR2 and HCDR3 shown in SEQ ID NO: 73, SEQ ID NO: 74 and SEQ ID NO: 21, respectively.

2. The anti-B7-H4 antibody or antigen-binding fragment thereof according to claim 1, wherein the antibody or antigen-binding fragment thereof is selected from the group consisting of murine antibody or fragment thereof, chimeric antibody or fragment thereof, and humanized antibody or fragment thereof.

3. The anti-B7-H4 antibody or antigen-binding fragment thereof according to claim 2, wherein the antibody heavy chain variable region further comprises heavy chain constant region(s) of human IgG1, IgG2, IgG3 or IgG4 or a variant thereof.

4. The anti-B7-H4 antibody or antigen-binding fragment thereof of claim 2, wherein the antibody light chain variable region is a light chain variable region comprising a sequence selected from the group consisting of: SEQ ID NO: 76, SEQ ID NO: 78, SEQ ID NO: 80 and SEQ ID NO: 82.

5. The anti-B7-H4 antibody or antigen-binding fragment thereof of claim 2, wherein the antibody heavy chain variable region is a heavy chain variable region comprising a sequence selected from the group consisting of: SEQ ID NO: 75, SEQ ID NO: 77, SEQ ID NO: 79 and SEQ ID NO: 81.

6. The anti-B7-H4 antibody or antigen-binding fragment thereof according to claim 2, wherein the antibody light chain is a light chain comprising a sequence selected from the group consisting of: SEQ ID NO: 84, SEQ ID NO: 86, SEQ ID NO: 88 and SEQ ID NO: 90.

7. The anti-B7-H4 antibody or antigen-binding fragment thereof according to claim 2, wherein the antibody heavy chain is a heavy chain comprising a sequence selected from the group consisting of: SEQ ID NO: 83, SEQ ID NO: 85, SEQ ID NO: 87 and SEQ ID NO: 89.

8. The anti-B7-H4 antibody or antigen-binding fragment thereof according to claim 2, comprising:
(1) a light chain variable region of SEQ ID NO: 76 and a heavy chain variable region of SEQ ID NO: 75;
(2) a light chain variable region of SEQ ID NO: 78 and a heavy chain variable region of SEQ ID NO: 77;
(3) a light chain variable region of SEQ ID NO: 80 and a heavy chain variable region of SEQ ID NO: 79; or
(4) a light chain variable region of SEQ ID NO: 82 and a heavy chain variable region of SEQ ID NO: 81.

9. The anti-B7-H4 antibody or antigen-binding fragment thereof of claim 2, comprising:
(1) a light chain of SEQ ID NO: 84 and a heavy chain of SEQ ID NO: 83;
(2) a light chain of SEQ ID NO: 86 and a heavy chain of SEQ ID NO: 85;
(3) a light chain of SEQ ID NO: 88 and a heavy chain of SEQ ID NO: 87; or
(4) a light chain of SEQ ID NO: 90 and a heavy chain of SEQ ID NO: 89.

10. The anti-B7-H4 antibody or antigen-binding fragment thereof according to claim 1, wherein the antibody or antigen-binding fragment thereof comprises at least one of the following characteristics: (1) binding to an epitope comprising amino acids 41-60 in SEQ ID NO: 100 of B7-H4; and (2) binding to an epitope comprising amino acids 53-59 in SEQ ID NO: 100 of B7-H4.

11. The anti-B7-H4 antibody or antigen-binding fragment thereof of claim 10, having at least one of the following characteristics: (1) binding to an epitope comprising amino acid 53 in SEQ ID NO: 100 of B7-H4; (2) binding to an epitope comprising amino acid 54 in SEQ ID NO: 100 of B7-H4; (3) binding to an epitope comprising amino acid 56 in SEQ ID NO: 100 of B7-H4; (4) binding to an epitope comprising amino acid 57 in SEQ ID NO: 100 of B7-H4; (5) binding to an epitope comprising amino acid 58 in SEQ ID NO: 100 of B7-H4; and (6) binding to an epitope comprising amino acid 59 in SEQ ID NO: 100 of B7-H4.

12. A DNA sequence, encoding the antibody or antigen-binding fragment of claim 1.

13. An expression vector, comprising the DNA sequence of claim 12.

14. A host cell, transformed with or comprising the expression vector of claim 13.

15. The host cell according to claim 14, wherein said host cell is bacterium, yeast, and Mammalian cell.

16. A method of producing an antibody comprising: culturing the host cell of claim 14, isolating the antibody from the culture, and purifying the antibody.

17. A pharmaceutical composition comprising the anti-B7-H4 antibody or antigen-binding fragment thereof of claim 1, and a pharmaceutically acceptable excipient, diluent or carrier.

18. A detection or diagnostic reagent, comprising the anti-B7-H4 antibody or antigen-binding fragment thereof of claim 1.

19. A method for treating B7-H4 mediated cancer, comprising administering to a subject in need thereof a pharmaceutically acceptable amount of the anti-B7-H4 antibody or antigen-binding fragment thereof according to claim 1.

20. The method of claim 19, wherein the cancer is selected from the group consisting of breast cancer, ovarian cancer, prostate cancer, pancreatic cancer, kidney cancer, lung cancer, liver cancer, stomach cancer, colon cancer, bladder cancer, esophageal cancer, cervical cancer, gallbladder cancer, glioblastoma and melanoma.

21. The anti-B7-H4 antibody or antigen-binding fragment thereof according to claim 1, wherein the anti-B7-H4 antibody or antigen-binding fragment thereof comprises a light chain variable region of SEQ ID NO: 76 and a heavy chain variable region of SEQ ID NO: 75.

\* \* \* \* \*

SEQUENCE LISTING

<160> NUMBER OF SEQ ID NOS: 111

<210> SEQ ID NO 1
<211> LENGTH: 120
<212> TYPE: PRT
<213> ORGANISM: Mus musculus

<400> SEQUENCE: 1

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Tyr Met Ser Trp Val Arg Gln Thr Pro Glu Lys Arg Leu Glu Trp Val
        35                  40                  45

Ala Tyr Val Ser Ser Gly Gly Gly Ser Thr Tyr Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Pro Glu Asp Thr Ala Met Tyr Tyr Cys
                85                  90                  95

Thr Arg Glu Ser Tyr Ser Gln Gly Asn Tyr Phe Asp Tyr Trp Gly Gln
            100                 105                 110

Gly Thr Thr Leu Thr Val Ser Ser
            115                 120

<210> SEQ ID NO 2
<211> LENGTH: 107
<212> TYPE: PRT
<213> ORGANISM: Mus musculus

<400> SEQUENCE: 2

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Ser Leu
                85                  90                  95

Thr Phe Gly Ala Gly Thr Lys Leu Glu Leu Lys
            100                 105

<210> SEQ ID NO 3
<211> LENGTH: 10
<212> TYPE: PRT
<213> ORGANISM: Mus musculus

<400> SEQUENCE: 3

Gly Phe Thr Phe Ser Asn Tyr Tyr Met Ser
1               5                   10

<210> SEQ ID NO 4
<211> LENGTH: 17
<212> TYPE: PRT
<213> ORGANISM: Mus musculus

<400> SEQUENCE: 4

Tyr Val Ser Ser Gly Gly Gly Ser Thr Tyr Tyr Ser Asp Ser Val Lys
1               5                   10                  15

Gly

<210> SEQ ID NO 5
<211> LENGTH: 11
<212> TYPE: PRT
<213> ORGANISM: Mus musculus

<400> SEQUENCE: 5

Glu Ser Tyr Ser Gln Gly Asn Tyr Phe Asp Tyr
1               5                   10

<210> SEQ ID NO 6
<211> LENGTH: 11
<212> TYPE: PRT
<213> ORGANISM: Mus musculus

<400> SEQUENCE: 6

Arg Ala Ser Gln Ser Ile Ser Asp Tyr Leu His
1               5                   10

<210> SEQ ID NO 7
<211> LENGTH: 7
<212> TYPE: PRT
<213> ORGANISM: Mus musculus

<400> SEQUENCE: 7

Phe Ala Ser Gln Ser Ile Ser
1               5

<210> SEQ ID NO 8
<211> LENGTH: 9
<212> TYPE: PRT
<213> ORGANISM: Mus musculus

<400> SEQUENCE: 8

Gln Asn Gly His Ser Phe Ser Leu Thr
1               5

<210> SEQ ID NO 9
<211> LENGTH: 123
<212> TYPE: PRT
<213> ORGANISM: Mus musculus

<400> SEQUENCE: 9

Glu Ile Gln Leu Gln Gln Ser Gly Pro Glu Leu Val Met Pro Gly Ala
1               5                   10                  15

Ser Val Lys Val Ser Cys Thr Ala Ser Gly Tyr Pro Phe Thr Thr Tyr
            20                  25                  30

Asn Met Tyr Trp Val Lys Gln Ser His Gly Lys Ser Leu Glu Trp Ile
        35                  40                  45

Ala Tyr Ile Asp Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Ser Gly Phe Tyr Asp Gly Tyr Tyr Ala Trp Tyr Phe Asp Val
            100                 105                 110

Trp Gly Ala Gly Thr Thr Val Thr Val Ser Ser
        115                 120

<210> SEQ ID NO 10
<211> LENGTH: 112
<212> TYPE: PRT
<213> ORGANISM: Mus musculus

<400> SEQUENCE: 10

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Gly Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110
```

<210> SEQ ID NO 11
<211> LENGTH: 10
<212> TYPE: PRT
<213> ORGANISM: Mus musculus

<400> SEQUENCE: 11

```
Gly Tyr Pro Phe Thr Thr Tyr Asn Met Tyr
1               5                   10
```

<210> SEQ ID NO 12
<211> LENGTH: 17
<212> TYPE: PRT
<213> ORGANISM: Mus musculus

<400> SEQUENCE: 12

```
Tyr Ile Asp Pro Tyr Asn Gly Gly Thr Ser Tyr Asn Gln Lys Phe Lys
1               5                   10                  15

Gly
```

<210> SEQ ID NO 13
<211> LENGTH: 14
<212> TYPE: PRT
<213> ORGANISM: Mus musculus

<400> SEQUENCE: 13

```
Ser Gly Phe Tyr Asp Gly Tyr Tyr Ala Trp Tyr Phe Asp Val
1               5                   10
```

<210> SEQ ID NO 14
<211> LENGTH: 16
<212> TYPE: PRT
<213> ORGANISM: Mus musculus

<400> SEQUENCE: 14

```
Arg Ser Ser Gln Ser Leu Val His Ser Gly Gly Asn Thr Tyr Leu His
1               5                   10                  15
```

<210> SEQ ID NO 15
<211> LENGTH: 7
<212> TYPE: PRT
<213> ORGANISM: Mus musculus

<400> SEQUENCE: 15

```
Lys Val Ser Asn Arg Phe Ser
1               5
```

```
<210> SEQ ID NO 16
<211> LENGTH: 9
<212> TYPE: PRT
<213> ORGANISM: Mus musculus

<400> SEQUENCE: 16

Ser Gln Ser Thr His Val Pro Leu Thr
1               5

<210> SEQ ID NO 17
<211> LENGTH: 115
<212> TYPE: PRT
<213> ORGANISM: Mus musculus

<400> SEQUENCE: 17

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Asn Ser
            20                  25                  30

Trp Met Asn Trp Ala Lys Leu Arg Pro Gly Gln Gly Leu Glu Trp Ile
        35                  40                  45

Gly Gly Ile Tyr Pro Asn Ser Gly Asn Ile Glu Tyr Asn Glu Lys Phe
    50                  55                  60

Lys Gly Lys Ala Thr Leu Thr Val Asp Thr Ser Ser Ser Thr Ala Tyr
65                  70                  75                  80

Met Asp Leu Thr Ser Leu Thr Ser Glu Asp Ser Ala Val Tyr Tyr Cys
                85                  90                  95

Ala Arg Asp Ser Arg Phe Ser Tyr Trp Gly Gln Gly Thr Leu Val Thr
            100                 105                 110

Val Ser Ala
        115

<210> SEQ ID NO 18
<211> LENGTH: 107
<212> TYPE: PRT
<213> ORGANISM: Mus musculus

<400> SEQUENCE: 18

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Arg Thr Ala
            20                  25                  30

Val Ala Trp Tyr Gln Gln Lys Pro Gly Gln Ser Pro Lys Leu Leu Ile
        35                  40                  45

Ser Ser Thr Ser Tyr Arg Tyr Thr Gly Val Pro Asp Arg Phe Thr Gly
    50                  55                  60

Ser Gly Ser Gly Thr Asp Phe Thr Phe Ile Ile Ser Ser Val Gln Ala
65                  70                  75                  80

Glu Asp Leu Ala Val Tyr Tyr Cys Gln Gln His Tyr Ser Thr Pro Leu
                85                  90                  95

Thr Phe Gly Ala Gly Thr Lys Leu Glu Leu Lys
            100                 105

<210> SEQ ID NO 19
<211> LENGTH: 10
<212> TYPE: PRT
<213> ORGANISM: Mus musculus

<400> SEQUENCE: 19
```

```
Gly Tyr Thr Phe Thr Asn Ser Trp Met Asn
1               5                   10
```

<210> SEQ ID NO 20
<211> LENGTH: 17
<212> TYPE: PRT
<213> ORGANISM: Mus musculus

<400> SEQUENCE: 20

```
Gly Ile Tyr Pro Asn Ser Gly Asn Ile Glu Tyr Asn Glu Lys Phe Lys
1               5                   10                  15

Gly
```

<210> SEQ ID NO 21
<211> LENGTH: 6
<212> TYPE: PRT
<213> ORGANISM: Mus musculus

<400> SEQUENCE: 21

```
Asp Ser Arg Phe Ser Tyr
1               5
```

<210> SEQ ID NO 22
<211> LENGTH: 11
<212> TYPE: PRT
<213> ORGANISM: Mus musculus

<400> SEQUENCE: 22

```
Lys Ala Ser Gln Asp Val Arg Thr Ala Val Ala
1               5                   10
```

<210> SEQ ID NO 23
<211> LENGTH: 7
<212> TYPE: PRT
<213> ORGANISM: Mus musculus

<400> SEQUENCE: 23

```
Ser Thr Ser Tyr Arg Tyr Thr
1               5
```

<210> SEQ ID NO 24
<211> LENGTH: 9
<212> TYPE: PRT
<213> ORGANISM: Mus musculus

<400> SEQUENCE: 24

```
Gln Gln His Tyr Ser Thr Pro Leu Thr
1               5
```

<210> SEQ ID NO 25
<211> LENGTH: 115
<212> TYPE: PRT
<213> ORGANISM: Mus musculus

<400> SEQUENCE: 25

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Leu Thr Phe Ser Arg Tyr
                20                  25                  30

Ala Met Ser Trp Val Arg Gln Thr Pro Glu Lys Arg Leu Glu Trp Val
            35                  40                  45

Ala Gly Ile Ser Ser Gly Gly Ser Tyr Thr Tyr Tyr Ser Asp Thr Val
        50                  55                  60
```

```
Lys Gly Arg Phe Thr Ile Ser Arg Asp Asn Val Asn Thr Leu Tyr
 65                  70                  75                  80

Leu Gln Met Ser Ser Leu Arg Ser Glu Asp Thr Ala Met Tyr Tyr Cys
                 85                  90                  95

Gly Arg Glu Tyr Gly Arg Asp Tyr Trp Gly Gln Gly Thr Ser Val Thr
            100                 105                 110

Val Ser Ser
        115

<210> SEQ ID NO 26
<211> LENGTH: 107
<212> TYPE: PRT
<213> ORGANISM: Mus musculus

<400> SEQUENCE: 26

Asp Ile Leu Met Thr Gln Ser Pro Ser Ser Met Ser Val Ser Leu Gly
  1               5                  10                  15

Asp Thr Val Ser Ile Thr Cys His Ala Ser Gln Gly Ile Asn Ser Asn
                 20                  25                  30

Ile Gly Trp Leu Gln Gln Lys Pro Gly Lys Ser Phe Lys Gly Leu Ile
             35                  40                  45

Tyr His Gly Thr Asn Leu Glu Asp Gly Val Pro Ser Arg Phe Ser Gly
         50                  55                  60

Ser Gly Ser Gly Thr Asp Tyr Ser Leu Thr Ile Ser Ser Leu Glu Ser
 65                  70                  75                  80

Glu Asp Phe Ala Asp Tyr Tyr Cys Val Gln Tyr Ala Gln Phe Pro Arg
                 85                  90                  95

Thr Phe Gly Gly Gly Thr Thr Leu Glu Ile Lys
            100                 105

<210> SEQ ID NO 27
<211> LENGTH: 10
<212> TYPE: PRT
<213> ORGANISM: Mus musculus

<400> SEQUENCE: 27

Gly Leu Thr Phe Ser Arg Tyr Ala Met Ser
  1               5                  10

<210> SEQ ID NO 28
<211> LENGTH: 17
<212> TYPE: PRT
<213> ORGANISM: Mus musculus

<400> SEQUENCE: 28

Gly Ile Ser Ser Gly Gly Ser Tyr Thr Tyr Tyr Ser Asp Thr Val Lys
  1               5                  10                  15

Gly

<210> SEQ ID NO 29
<211> LENGTH: 6
<212> TYPE: PRT
<213> ORGANISM: Mus musculus

<400> SEQUENCE: 29

Glu Tyr Gly Arg Asp Tyr
  1               5

<210> SEQ ID NO 30
```

```
-continued

<211> LENGTH: 11
<212> TYPE: PRT
<213> ORGANISM: Mus musculus

<400> SEQUENCE: 30

His Ala Ser Gln Gly Ile Asn Ser Asn Ile Gly
1               5                   10

<210> SEQ ID NO 31
<211> LENGTH: 7
<212> TYPE: PRT
<213> ORGANISM: Mus musculus

<400> SEQUENCE: 31

His Gly Thr Asn Leu Glu Asp
1               5

<210> SEQ ID NO 32
<211> LENGTH: 9
<212> TYPE: PRT
<213> ORGANISM: Mus musculus

<400> SEQUENCE: 32

Val Gln Tyr Ala Gln Phe Pro Arg Thr
1               5

<210> SEQ ID NO 33
<211> LENGTH: 113
<212> TYPE: PRT
<213> ORGANISM: Mus musculus

<400> SEQUENCE: 33

Glu Val Gln Leu Val Glu Ser Gly Gly Gly Phe Val Lys Pro Gly Gly
1               5                   10                  15

Ser Leu Lys Leu Ser Cys Ala Ala Ser Gly Phe Thr Phe Ser Thr Phe
                20                  25                  30

Gly Met Ser Trp Val Arg Gln Thr Pro Asp Lys Arg Leu Glu Trp Val
            35                  40                  45

Ala Gly Ile Ser Pro Gly Gly Ser Tyr Thr Tyr Tyr Pro Asp Thr Val
        50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Ser Ala Met Tyr Tyr Cys
                85                  90                  95

Thr Arg Gly Arg Ser Val Trp Gly Thr Gly Thr Thr Val Thr Val Ser
            100                 105                 110

Ser

<210> SEQ ID NO 34
<211> LENGTH: 107
<212> TYPE: PRT
<213> ORGANISM: Mus musculus

<400> SEQUENCE: 34

Asp Ile Leu Met Thr Gln Ser Pro Ser Ser Met Ser Val Ser Leu Gly
1               5                   10                  15

Asp Thr Val Ser Ile Thr Cys His Ala Ser Gln Asp Ile Ser Ser Asn
                20                  25                  30

Ile Gly Trp Leu Gln Gln Lys Pro Gly Lys Ser Phe Lys Gly Leu Ile
            35                  40                  45
```

```
Tyr His Gly Thr Thr Leu Glu Asp Gly Ile Pro Ser Arg Phe Ser Gly
         50                  55                  60

Ser Gly Ser Gly Ala Asp Tyr Ser Leu Thr Ile Ser Ser Leu Glu Ser
 65                  70                  75                  80

Glu Asp Phe Ala Asp Tyr Tyr Cys Val Gln Ser Ala Gln Phe Pro Trp
                 85                  90                  95

Thr Phe Gly Gly Gly Thr Lys Leu Glu Ile Lys
            100                 105

<210> SEQ ID NO 35
<211> LENGTH: 10
<212> TYPE: PRT
<213> ORGANISM: Mus musculus

<400> SEQUENCE: 35

Gly Phe Thr Phe Ser Thr Phe Gly Met Ser
 1               5                  10

<210> SEQ ID NO 36
<211> LENGTH: 17
<212> TYPE: PRT
<213> ORGANISM: Mus musculus

<400> SEQUENCE: 36

Gly Ile Ser Pro Gly Gly Ser Tyr Thr Tyr Tyr Pro Asp Thr Val Lys
 1               5                  10                  15

Gly

<210> SEQ ID NO 37
<211> LENGTH: 4
<212> TYPE: PRT
<213> ORGANISM: Mus musculus

<400> SEQUENCE: 37

Gly Arg Ser Val
 1

<210> SEQ ID NO 38
<211> LENGTH: 11
<212> TYPE: PRT
<213> ORGANISM: Mus musculus

<400> SEQUENCE: 38

His Ala Ser Gln Asp Ile Ser Ser Asn Ile Gly
 1               5                  10

<210> SEQ ID NO 39
<211> LENGTH: 7
<212> TYPE: PRT
<213> ORGANISM: Mus musculus

<400> SEQUENCE: 39

His Gly Thr Thr Leu Glu Asp
 1               5

<210> SEQ ID NO 40
<211> LENGTH: 9
<212> TYPE: PRT
<213> ORGANISM: Mus musculus

<400> SEQUENCE: 40

Val Gln Ser Ala Gln Phe Pro Trp Thr
 1               5
```

<210> SEQ ID NO 41
<211> LENGTH: 115
<212> TYPE: PRT
<213> ORGANISM: Mus musculus

<400> SEQUENCE: 41

Gln Val Gln Leu Gln Gln Pro Gly Ser Val Leu Val Arg Pro Gly Thr
1               5                   10                  15

Ser Val Lys Leu Ser Cys Lys Ala Ser Gly Tyr Thr Phe Thr Ser Ser
            20                  25                  30

Trp Met Asn Trp Val Lys Gln Arg Pro Gly Gln Gly Leu Glu Trp Ile
        35                  40                  45

Gly Gly Ile Tyr Pro Asn Arg Gly Thr Thr Glu Tyr Asn Glu Lys Phe
    50                  55                  60

Lys Gly Lys Ala Thr Leu Thr Val Asp Thr Ser Ser Ser Thr Ala Phe
65                  70                  75                  80

Met Asp Leu Asn Arg Leu Thr Ser Glu Asp Ser Ala Val Tyr Tyr Cys
                85                  90                  95

Ala Arg Asp Ser Arg Phe Ala Asp Trp Gly Gln Gly Thr Leu Val Thr
            100                 105                 110

Val Ser Ala
        115

<210> SEQ ID NO 42
<211> LENGTH: 107
<212> TYPE: PRT
<213> ORGANISM: Mus musculus

<400> SEQUENCE: 42

Asp Ile Met Leu Thr Gln Ser His Lys Phe Met Ser Thr Ser Val Gly
1               5                   10                  15

Asp Arg Val Ser Ile Thr Cys Lys Ala Ser Gln Asp Val Ser Ala Ala
            20                  25                  30

Val Ala Trp Tyr Gln Gln Lys Pro Gly Gln Ser Pro Lys Leu Leu Ile
        35                  40                  45

Ser Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Asn Thr Pro Leu
                85                  90                  95

Thr Phe Gly Ala Gly Thr Lys Leu Glu Leu Lys
            100                 105

<210> SEQ ID NO 43
<211> LENGTH: 10
<212> TYPE: PRT
<213> ORGANISM: Mus musculus

<400> SEQUENCE: 43

Gly Tyr Thr Phe Thr Ser Ser Trp Met Asn
1               5                   10

<210> SEQ ID NO 44
<211> LENGTH: 17
<212> TYPE: PRT
<213> ORGANISM: Mus musculus -continued

```
<400> SEQUENCE: 44

Gly Ile Tyr Pro Asn Arg Gly Thr Thr Glu Tyr Asn Glu Lys Phe Lys
1               5                   10                  15

Gly

<210> SEQ ID NO 45
<211> LENGTH: 6
<212> TYPE: PRT
<213> ORGANISM: Mus musculus

<400> SEQUENCE: 45

Asp Ser Arg Phe Ala Asp
1               5

<210> SEQ ID NO 46
<211> LENGTH: 11
<212> TYPE: PRT
<213> ORGANISM: Mus musculus

<400> SEQUENCE: 46

Lys Ala Ser Gln Asp Val Ser Ala Ala Val Ala
1               5                   10

<210> SEQ ID NO 47
<211> LENGTH: 7
<212> TYPE: PRT
<213> ORGANISM: Mus musculus

<400> SEQUENCE: 47

Ser Ala Ser Tyr Arg Tyr Thr
1               5

<210> SEQ ID NO 48
<211> LENGTH: 9
<212> TYPE: PRT
<213> ORGANISM: Mus musculus
<220> FEATURE:
<221> NAME/KEY: DOMAIN
<222> LOCATION: (1)..(10)
<223> OTHER INFORMATION: mutated 2F8 HCDR1 region

<400> SEQUENCE: 48

Gln Gln His Tyr Asn Thr Pro Leu Thr
1               5

<210> SEQ ID NO 49
<211> LENGTH: 118
<212> TYPE: PRT
<213> ORGANISM: Mus musculus

<400> SEQUENCE: 49

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Arg Tyr
            20                  25                  30

Ala Met Ser Trp Val Arg Gln Thr Pro Glu Lys Arg Leu Glu Trp Val
        35                  40                  45

Ala Gly Ile Ser Ser Gly Gly Ser Tyr Thr Tyr Tyr Pro Asp Thr Leu
    50                  55                  60

Lys Gly Arg Phe Thr Val Ser Arg Asp Asn Ala Arg Asn Thr Leu Tyr
65                  70                  75                  80

Leu Gln Met Ser Ser Leu Arg Ser Glu Asp Thr Ala Lys Tyr Phe Cys
```

```
                    85                  90                  95
Ala Ser Gln Gly Ser Asn His Tyr Phe Asp Tyr Trp Gly Gln Gly Thr
                100                 105                 110

Thr Leu Thr Val Ser Ser
            115

<210> SEQ ID NO 50
<211> LENGTH: 107
<212> TYPE: PRT
<213> ORGANISM: Mus musculus

<400> SEQUENCE: 50

Asp Thr Leu Met Thr Gln Ser Pro Ser Ser Met Ser Val Ser Leu Gly
1               5                   10                  15

Asp Thr Val Ser Ile Thr Cys His Ala Ser Gln Gly Ile His Asn Asn
                20                  25                  30

Ile Gly Trp Leu Gln Gln Lys Pro Gly Lys Ser Phe Lys Ala Leu Ile
            35                  40                  45

Tyr His Gly Thr Asn Leu Glu Asp Gly Val Pro Ser Arg Phe Ser Gly
        50                  55                  60

Ser Gly Ser Gly Ala Asp Tyr Ser Leu Ile Ile Ser Ser Leu Glu Ser
65                  70                  75                  80

Glu Asp Phe Ala Asp Tyr Tyr Cys Val Gln Tyr Ala Gln Phe Pro Tyr
                85                  90                  95

Thr Phe Gly Gly Gly Thr Lys Leu Glu Ile Lys
                100                 105

<210> SEQ ID NO 51
<211> LENGTH: 10
<212> TYPE: PRT
<213> ORGANISM: Mus musculus

<400> SEQUENCE: 51

Gly Phe Thr Phe Ser Arg Tyr Ala Met Ser
1               5                   10

<210> SEQ ID NO 52
<211> LENGTH: 17
<212> TYPE: PRT
<213> ORGANISM: Mus musculus

<400> SEQUENCE: 52

Gly Ile Ser Ser Gly Gly Ser Tyr Thr Tyr Tyr Pro Asp Thr Leu Lys
1               5                   10                  15

Gly

<210> SEQ ID NO 53
<211> LENGTH: 9
<212> TYPE: PRT
<213> ORGANISM: Mus musculus

<400> SEQUENCE: 53

Gln Gly Ser Asn His Tyr Phe Asp Tyr
1               5

<210> SEQ ID NO 54
<211> LENGTH: 11
<212> TYPE: PRT
<213> ORGANISM: Mus musculus

<400> SEQUENCE: 54
```

His Ala Ser Gln Gly Ile His Asn Asn Ile Gly
1               5                   10

<210> SEQ ID NO 55
<211> LENGTH: 7
<212> TYPE: PRT
<213> ORGANISM: Mus musculus

<400> SEQUENCE: 55

His Gly Thr Asn Leu Glu Asp
1               5

<210> SEQ ID NO 56
<211> LENGTH: 9
<212> TYPE: PRT
<213> ORGANISM: Mus musculus

<400> SEQUENCE: 56

Val Gln Tyr Ala Gln Phe Pro Tyr Thr
1               5

<210> SEQ ID NO 57
<211> LENGTH: 118
<212> TYPE: PRT
<213> ORGANISM: Mus musculus

<400> SEQUENCE: 57

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Arg Tyr
                20                  25                  30

Gly Met Ser Trp Val Arg Gln Thr Pro Glu Lys Arg Leu Glu Trp Val
            35                  40                  45

Ala Gly Ile Asn Gly Gly Gly Ser Tyr Thr Tyr Tyr Leu Asp Thr Val
        50                  55                  60

Lys Gly Arg Phe Thr Ile Ser Arg Asp Asn Ser Arg Asn Thr Leu Tyr
65                  70                  75                  80

Leu Gln Met Ser Ser Leu Arg Ser Glu Asp Thr Ala Met Tyr Tyr Cys
                85                  90                  95

Val Ser Gln Gly Ser Asn Tyr Tyr Phe Asp Tyr Trp Gly Gln Gly Thr
            100                 105                 110

Thr Leu Thr Val Ser Ser
        115

<210> SEQ ID NO 58
<211> LENGTH: 107
<212> TYPE: PRT
<213> ORGANISM: Mus musculus

<400> SEQUENCE: 58

Asp Ile Arg Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
                20                  25                  30

Ile Gly Trp Leu Gln Gln Lys Pro Gly Lys Ser Phe Lys Ala Leu Ile
            35                  40                  45

Tyr His Gly Thr Asn Leu Glu Asp Gly Val Pro Ser Arg Phe Ser Gly
        50                  55                  60

Ser Gly Ser Gly Ala Asp Tyr Ser Leu Thr Ile Ser Ser Leu Glu Ser

```
            65                  70                  75                  80
Glu Asp Phe Ala Asp Tyr Tyr Cys Val Gln Tyr Ala Gln Phe Pro Tyr
                    85                  90                  95
Thr Phe Gly Gly Gly Thr Lys Leu Glu Ile Lys
            100                 105

<210> SEQ ID NO 59
<211> LENGTH: 10
<212> TYPE: PRT
<213> ORGANISM: Mus musculus

<400> SEQUENCE: 59

Gly Phe Thr Phe Ser Arg Tyr Gly Met Ser
1               5                   10

<210> SEQ ID NO 60
<211> LENGTH: 17
<212> TYPE: PRT
<213> ORGANISM: Mus musculus

<400> SEQUENCE: 60

Gly Ile Asn Gly Gly Gly Ser Tyr Thr Tyr Tyr Leu Asp Thr Val Lys
1               5                   10                  15
Gly

<210> SEQ ID NO 61
<211> LENGTH: 9
<212> TYPE: PRT
<213> ORGANISM: Mus musculus

<400> SEQUENCE: 61

Gln Gly Ser Asn Tyr Tyr Phe Asp Tyr
1               5

<210> SEQ ID NO 62
<211> LENGTH: 11
<212> TYPE: PRT
<213> ORGANISM: Mus musculus

<400> SEQUENCE: 62

His Ala Ser Gln Gly Ile Ser Ser Asn Ile Gly
1               5                   10

<210> SEQ ID NO 63
<211> LENGTH: 7
<212> TYPE: PRT
<213> ORGANISM: Mus musculus

<400> SEQUENCE: 63

His Gly Thr Asn Leu Glu Asp
1               5

<210> SEQ ID NO 64
<211> LENGTH: 9
<212> TYPE: PRT
<213> ORGANISM: Mus musculus

<400> SEQUENCE: 64

Val Gln Tyr Ala Gln Phe Pro Tyr Thr
1               5

<210> SEQ ID NO 65
<211> LENGTH: 115
```

```
<212> TYPE: PRT
<213> ORGANISM: Mus musculus

<400> SEQUENCE: 65

Gln Val Gln Leu Gln Gln Pro Gly Ser Val Leu Val Arg Pro Gly Ala
1               5                   10                  15

Ser Val Lys Leu Ser Cys Lys Ala Ser Gly Asp Thr Phe Thr Thr Tyr
            20                  25                  30

Trp Met Asn Trp Val Lys Gln Arg Pro Gly Gln Gly Leu Glu Trp Ile
        35                  40                  45

Gly Gly Ile Tyr Leu Asn Ser Gly Ser Ser Glu Tyr Asn Glu Lys Phe
    50                  55                  60

Lys Gly Lys Ala Thr Leu Ser Val Asp Thr Ser Ser Ser Thr Ala Tyr
65                  70                  75                  80

Met Asp Leu Ser Ser Leu Thr Ser Glu Asp Ser Ala Val Tyr Tyr Cys
                85                  90                  95

Ala Arg Asp Ser Arg Phe Ser Tyr Trp Gly Gln Gly Thr Leu Val Thr
            100                 105                 110

Val Ser Ala
        115

<210> SEQ ID NO 66
<211> LENGTH: 107
<212> TYPE: PRT
<213> ORGANISM: Mus musculus

<400> SEQUENCE: 66

Asp Ile Val Met Thr Gln Ser His Lys Phe Leu Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Glu Leu Leu Ile
        35                  40                  45

Ser Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Asn Thr Pro Leu
                85                  90                  95

Thr Phe Gly Ala Gly Thr Gln Leu Glu Leu Lys
            100                 105

<210> SEQ ID NO 67
<211> LENGTH: 7
<212> TYPE: PRT
<213> ORGANISM: Mus musculus

<400> SEQUENCE: 67

Gly Asp Thr Phe Thr Thr Tyr
1               5

<210> SEQ ID NO 68
<211> LENGTH: 6
<212> TYPE: PRT
<213> ORGANISM: Mus musculus

<400> SEQUENCE: 68

Tyr Leu Asn Ser Gly Ser
1               5
```

<210> SEQ ID NO 69
<211> LENGTH: 6
<212> TYPE: PRT
<213> ORGANISM: Mus musculus

<400> SEQUENCE: 69

Asp Ser Arg Phe Ser Tyr
1               5

<210> SEQ ID NO 70
<211> LENGTH: 11
<212> TYPE: PRT
<213> ORGANISM: Mus musculus

<400> SEQUENCE: 70

Lys Ala Ser Gln Asp Val Ser Thr Ala Val Ala
1               5                   10

<210> SEQ ID NO 71
<211> LENGTH: 7
<212> TYPE: PRT
<213> ORGANISM: Mus musculus

<400> SEQUENCE: 71

Ser Ala Ser Tyr Arg Tyr Thr
1               5

<210> SEQ ID NO 72
<211> LENGTH: 9
<212> TYPE: PRT
<213> ORGANISM: Mus musculus

<400> SEQUENCE: 72

Gln Gln His Tyr Asn Thr Pro Leu Thr
1               5

<210> SEQ ID NO 73
<211> LENGTH: 10
<212> TYPE: PRT
<213> ORGANISM: Artificial Sequence
<220> FEATURE:
<221> NAME/KEY: DOMAIN
<222> LOCATION: (1)..(10)
<223> OTHER INFORMATION: humanized 2F8 HCDR1

<400> SEQUENCE: 73

Gly Tyr Thr Phe Thr Ser Ser Trp Met Asn
1               5                   10

<210> SEQ ID NO 74
<211> LENGTH: 17
<212> TYPE: PRT
<213> ORGANISM: Artificial Sequence
<220> FEATURE:
<221> NAME/KEY: DOMAIN
<222> LOCATION: (1)..(17)
<223> OTHER INFORMATION: humanized 2F8 HCDR2

<400> SEQUENCE: 74

Gly Ile Tyr Pro Asn Arg Gly Asn Ile Glu Tyr Asn Glu Lys Phe Lys
1               5                   10                  15

Gly

<210> SEQ ID NO 75

```
<211> LENGTH: 120
<212> TYPE: PRT
<213> ORGANISM: Artificial Sequence
<220> FEATURE:
<221> NAME/KEY: DOMAIN
<222> LOCATION: (1)..(120)
<223> OTHER INFORMATION: hu2F7 HCVR

<400> SEQUENCE: 75
```

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ala Tyr Val Ser Ser Gly Gly Gly Ser Thr Tyr Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Thr Arg Glu Ser Tyr Ser Gln Gly Asn Tyr Phe Asp Tyr Trp Gly Gln
            100                 105                 110

Gly Thr Thr Val Thr Val Ser Ser
        115                 120

```
<210> SEQ ID NO 76
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: hu2F7 LCVR

<400> SEQUENCE: 76
```

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp Tyr
            20                  25                  30

Leu His Trp Tyr Gln Gln Lys Pro Gly Gln Ser Pro Arg Leu Leu Ile
        35                  40                  45

Lys Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Ser Leu
                85                  90                  95

Thr Phe Gly Gln Gly Thr Lys Leu Glu Ile Lys
            100                 105

```
<210> SEQ ID NO 77
<211> LENGTH: 115
<212> TYPE: PRT
<213> ORGANISM: Artificial Sequence
<220> FEATURE:
<221> NAME/KEY: DOMAIN
<222> LOCATION: (1)..(115)
<223> OTHER INFORMATION: hu2F8 HCVR

<400> SEQUENCE: 77
```

-continued

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met Asn Trp Val Arg Gln Ala Pro Gly Gln Arg Leu Glu Trp Met
        35                  40                  45

Gly Gly Ile Tyr Pro Asn Arg Gly Asn Ile Glu Tyr Asn Glu Lys Phe
    50                  55                  60

Lys Gly Arg Val Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Ser Arg Phe Ser Tyr Trp Gly Gln Gly Thr Leu Val Thr
            100                 105                 110

Val Ser Ser
        115

<210> SEQ ID NO 78
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: hu2F8 LCVR

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Thr Ala
            20                  25                  30

Val Ala Trp Tyr Gln Gln Lys Pro Gly Lys Ala Pro Lys Leu Leu Ile
        35                  40                  45

Ser Ser Thr Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Leu
            85                  90                  95

Thr Phe Gly Gly Gly Thr Lys Val Glu Ile Lys
            100                 105

<210> SEQ ID NO 79
<211> LENGTH: 118
<212> TYPE: PRT
<213> ORGANISM: Artificial Sequence
<220> FEATURE:
<221> NAME/KEY: DOMAIN
<222> LOCATION: (1)..(118)
<223> OTHER INFORMATION: hu2G6 HCVR

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Gly Ile Asn Gly Gly Gly Ser Tyr Thr Tyr Tyr Leu Asp Thr Val

```
                50                  55                  60
Lys Gly Arg Phe Thr Ile Ser Arg Asp Asn Ala Arg Asn Thr Leu Tyr
 65                  70                  75                  80

Leu Gln Met Ser Ser Leu Arg Ala Glu Asp Thr Ala Val Tyr Tyr Cys
                 85                  90                  95

Val Ser Gln Gly Ser Asn Tyr Tyr Phe Asp Tyr Trp Gly Gln Gly Thr
            100                 105                 110

Leu Val Thr Val Ser Ser
        115
```

<210> SEQ ID NO 80
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: hu2G6 LCVR

<400> SEQUENCE: 80

```
Asp Ile Arg Met Thr Gln Ser Pro Ser Ser Leu Ser Ala Ser Val Gly
 1               5                  10                  15

Asp Arg Val Thr Ile Thr Cys His Ala Ser Gln Gly Ile Ser Ser Asn
             20                  25                  30

Ile Gly Trp Leu Gln Gln Lys Pro Gly Lys Ala Pro Lys Ala Leu Ile
         35                  40                  45

Tyr His Gly Thr Asn Leu Glu Asp Gly Val Pro Ser Arg Phe Ser Gly
     50                  55                  60

Ser Gly Ser Gly Ala Asp Tyr Thr Leu Thr Ile Ser Ser Leu Gln Pro
 65                  70                  75                  80

Glu Asp Phe Ala Thr Tyr Tyr Cys Val Gln Tyr Ala Gln Phe Pro Tyr
                 85                  90                  95

Thr Phe Gly Gly Gly Thr Lys Val Glu Ile Lys
            100                 105
```

<210> SEQ ID NO 81
<211> LENGTH: 115
<212> TYPE: PRT
<213> ORGANISM: Artificial Sequence
<220> FEATURE:
<221> NAME/KEY: DOMAIN
<222> LOCATION: (1)..(115)
<223> OTHER INFORMATION: hu1C9 HCVR

<400> SEQUENCE: 81

```
Glu Val Gln Leu Val Gln Ser Gly Ala Glu Val Lys Lys Pro Gly Ala
 1               5                  10                  15

Ser Val Lys Val Ser Cys Lys Ala Ser Gly Asp Thr Phe Thr Thr Tyr
             20                  25                  30

Trp Met Asn Trp Val Arg Gln Ala Pro Gly Gln Arg Leu Glu Trp Met
         35                  40                  45

Gly Gly Ile Tyr Leu Asn Arg Gly Ser Glu Tyr Asn Glu Lys Phe
     50                  55                  60

Lys Gly Arg Val Thr Leu Thr Val Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ser Arg Phe Ser Tyr Trp Gly Gln Gly Thr Leu Val Thr
            100                 105                 110
```

```
Val Ser Ser
        115

<210> SEQ ID NO 82
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: hu1C9 LCVR

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Ser Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Asn Thr Pro Leu
                85                  90                  95

Thr Phe Gly Gly Gly Thr Lys Val Glu Ile Lys
            100                 105

<210> SEQ ID NO 83
<211> LENGTH: 450
<212> TYPE: PRT
<213> ORGANISM: Artificial Sequence
<220> FEATURE:
<221> NAME/KEY: DOMAIN
<222> LOCATION: (1)..(450)
<223> OTHER INFORMATION: hu2F7 HC

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ala Tyr Val Ser Ser Gly Gly Gly Ser Thr Tyr Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Thr Arg Glu Ser Tyr Ser Gln Gly Asn Tyr Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 84
<211> LENGTH: 214
<212> TYPE: PRT
<213> ORGANISM: Artificial Sequence
<220> FEATURE:
<221> NAME/KEY: DOMAIN
<222> LOCATION: (1)..(214)
<223> OTHER INFORMATION: hu2F7 LC

<400> SEQUENCE: 84

Glu Ile Val Met Thr Gln Ser Pro Ala Thr Leu Ser Leu Ser Pro Gly
1               5                   10                  15
Glu Arg Ala Thr Leu Ser Cys Arg Ala Ser Gln Ser Ile Ser Asp Tyr
            20                  25                  30
Leu His Trp Tyr Gln Gln Lys Pro Gly Gln Ser Pro Arg Leu Leu Ile
        35                  40                  45
Lys Phe Ala Ser Gln Ser Ile Ser Gly Ile Pro Ala Arg Phe Ser Gly
```

```
                50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Asn Gly His Ser Phe Ser Leu
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 85
<211> LENGTH: 445
<212> TYPE: PRT
<213> ORGANISM: Artificial Sequence
<220> FEATURE:
<221> NAME/KEY: DOMAIN
<222> LOCATION: (1)..(445)
<223> OTHER INFORMATION: hu2F8 HC

<400> SEQUENCE: 85

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Ser
             20                  25                  30

Trp Met Asn Trp Val Arg Gln Ala Pro Gly Gln Arg Leu Glu Trp Met
         35                  40                  45

Gly Gly Ile Tyr Pro Asn Arg Gly Asn Ile Glu Tyr Asn Glu Lys Phe
     50                  55                  60

Lys Gly Arg Val Thr Leu Thr Val Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ser Arg Phe Ser Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190
```

Thr Gln Thr Tyr Ile Cys Asn Val Asn His Lys Pro Ser Asn Thr Lys
                195                 200                 205
Val Asp Lys Lys Val Glu Pro Lys Ser Cys Asp Lys Thr His Thr Cys
210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
                260                 265                 270
Phe Asn Trp Tyr Val Asp Gly Val Glu Val His Asn Ala Lys Thr Lys
                275                 280                 285
Pro Arg Glu Glu Gln Tyr Asn Ser Thr Tyr Arg Val Val Ser Val Leu
                290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
                340                 345                 350
Arg Glu Glu Met Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
                370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
                420                 425                 430
His Tyr Thr Gln Lys Ser Leu Ser Leu Ser Pro Gly Lys
                435                 440                 445

<210> SEQ ID NO 86
<211> LENGTH: 214
<212> TYPE: PRT
<213> ORGANISM: Artificial Sequence
<220> FEATURE:
<221> NAME/KEY: DOMAIN
<222> LOCATION: (1)..(214)
<223> OTHER INFORMATION: hu2F8 LC

<400> SEQUENCE: 86

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Arg Thr Ala
                20                  25                  30
Val Ala Trp Tyr Gln Gln Lys Pro Gly Lys Ala Pro Lys Leu Leu Ile
                35                  40                  45
Ser Ser Thr Ser Tyr Arg Tyr Thr Gly Val Pro Ser Arg Phe Ser Gly
                50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Gln His Tyr Ser Thr Pro Leu
                85                  90                  95

```
Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 87
<211> LENGTH: 448
<212> TYPE: PRT
<213> ORGANISM: Artificial Sequence
<220> FEATURE:
<221> NAME/KEY: DOMAIN
<222> LOCATION: (1)..(448)
<223> OTHER INFORMATION: hu2G6 HC

<400> SEQUENCE: 87

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Gly Ile Asn Gly Gly Gly Ser Tyr Thr Tyr Tyr Leu Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ala Glu Asp Thr Ala Val Tyr Tyr Cys
                85                  90                  95

Val Ser Gln Gly Ser Asn Tyr Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
```

```
            225                 230                 235                 240
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 88
<211> LENGTH: 214
<212> TYPE: PRT
<213> ORGANISM: Artificial Sequence
<220> FEATURE:
<221> NAME/KEY: DOMAIN
<222> LOCATION: (1)..(214)
<223> OTHER INFORMATION: hu2G6 LC

<400> SEQUENCE: 88

Asp Ile Arg Met Thr Gln Ser Pro Ser Ser Leu Ser Ala Ser Val Gly
1               5                   10                  15

Asp Arg Val Thr Ile Thr Cys His Ala Ser Gln Gly Ile Ser Ser Asn
            20                  25                  30

Ile Gly Trp Leu Gln Gln Lys Pro Gly Lys Ala Pro Lys Ala Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 89
<211> LENGTH: 445
<212> TYPE: PRT
<213> ORGANISM: Artificial Sequence
<220> FEATURE:
<221> NAME/KEY: DOMAIN
<222> LOCATION: (1)..(445)
<223> OTHER INFORMATION: hu1C9 HC

<400> SEQUENCE: 89

```
Glu Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Thr Thr Tyr
            20                  25                  30

Trp Met Asn Trp Val Arg Gln Ala Pro Gly Gln Arg Leu Glu Trp Met
        35                  40                  45

Gly Gly Ile Tyr Leu Asn Arg Gly Ser Ser Glu Tyr Asn Glu Lys Phe
    50                  55                  60

Lys Gly Arg Val Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Arg Phe Ser Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270
```

```
Phe Asn Trp Tyr Val Asp Gly Val Glu Val His Asn Ala Lys Thr Lys
            275                 280                 285
Pro Arg Glu Glu Gln Tyr Asn Ser Thr Tyr Arg Val Val Ser Val Leu
        290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 90
<211> LENGTH: 214
<212> TYPE: PRT
<213> ORGANISM: Artificial Sequence
<220> FEATURE:
<221> NAME/KEY: DOMAIN
<222> LOCATION: (1)..(214)
<223> OTHER INFORMATION: hu1C9 LC

<400> SEQUENCE: 90

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Ser Ser Ala Ser Tyr Arg Tyr Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Gln His Tyr Asn Thr Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
```

```
              180                 185                 190
Ala Cys Glu Val Thr His Gln Gly Leu Ser Ser Pro Val Thr Lys Ser
        195                 200                 205

Phe Asn Arg Gly Glu Cys
    210

<210> SEQ ID NO 91
<211> LENGTH: 120
<212> TYPE: PRT
<213> ORGANISM: Artificial Sequence
<220> FEATURE:
<221> NAME/KEY: DOMAIN
<222> LOCATION: (1)..(120)
<223> OTHER INFORMATION: hu2F7 HCVR

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ala Tyr Val Ser Gly Gly Gly Ser Thr Tyr Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Glu Ser Tyr Ser Gln Gly Asn Tyr Phe Asp Tyr Trp Gly Gln
            100                 105                 110

Gly Thr Thr Val Thr Val Ser Ser
        115                 120

<210> SEQ ID NO 92
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: hu2F7 LCVR

<400> SEQUENCE: 92

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp Tyr
            20                  25                  30

Leu His Trp Tyr Gln Gln Lys Pro Gly Gln Ala Pro Arg Leu Leu Ile
        35                  40                  45

Tyr Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Ser Leu
                85                  90                  95

Thr Phe Gly Gln Gly Thr Lys Leu Glu Ile Lys
            100                 105

<210> SEQ ID NO 93
```

```
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: hu2F7 LCVR

<400> SEQUENCE: 93
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp Tyr
            20                  25                  30

Leu His Trp Tyr Gln Gln Lys Pro Gly Gln Ala Pro Arg Leu Leu Ile
        35                  40                  45

Lys Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Ser Leu
                85                  90                  95

Thr Phe Gly Gln Gly Thr Lys Leu Glu Ile Lys
            100                 105

```
<210> SEQ ID NO 94
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: hu2F7 LCVR

<400> SEQUENCE: 94
```

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp Tyr
            20                  25                  30

Leu His Trp Tyr Gln Gln Lys Pro Gly Gln Ala Pro Arg Leu Leu Ile
        35                  40                  45

Lys Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Ser Leu
                85                  90                  95

Thr Phe Gly Gln Gly Thr Lys Leu Glu Ile Lys
            100                 105

```
<210> SEQ ID NO 95
<211> LENGTH: 115
<212> TYPE: PRT
<213> ORGANISM: Artificial Sequence
<220> FEATURE:
<221> NAME/KEY: DOMAIN
<222> LOCATION: (1)..(115)
<223> OTHER INFORMATION: hu2F8 HCVR

<400> SEQUENCE: 95
```

Glu Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Ser Ser
            20                  25                  30

Trp Met Asn Trp Val Arg Gln Ala Pro Gly Gln Arg Leu Glu Trp Met
        35                  40                  45

Gly Gly Ile Tyr Pro Asn Arg Gly Asn Ile Glu Tyr Asn Glu Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Arg Phe Ser Tyr Trp Gly Gln Gly Thr Leu Val Thr
            100                 105                 110

Val Ser Ser
        115

<210> SEQ ID NO 96
<211> LENGTH: 115
<212> TYPE: PRT
<213> ORGANISM: Artificial Sequence
<220> FEATURE:
<221> NAME/KEY: DOMAIN
<222> LOCATION: (1)..(115)
<223> OTHER INFORMATION: hu2F8 HCVR

<400> SEQUENCE: 96

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met Asn Trp Val Arg Gln Ala Pro Gly Gln Gly Leu Glu Trp Met
        35                  40                  45

Gly Gly Ile Tyr Pro Asn Arg Gly Asn Ile Glu Tyr Asn Glu Lys Phe
    50                  55                  60

Lys Gly Arg Val Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Arg Phe Ser Tyr Trp Gly Gln Gly Thr Leu Val Thr
            100                 105                 110

Val Ser Ser
        115

<210> SEQ ID NO 97
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: hu2F8 LCVR

<400> SEQUENCE: 97

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Arg Thr Ala
            20                  25                  30

Val Ala Trp Tyr Gln Gln Lys Pro Gly Lys Ala Pro Lys Leu Leu Ile
        35                  40                  45

Ser Ser Thr Ser Tyr Arg Tyr Thr Gly Val Pro Ser Arg Phe Ser Gly
```

```
                50                  55                  60
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Tyr Ser Thr Pro Leu
                 85                  90                  95

Thr Phe Gly Gly Gly Thr Lys Val Glu Ile Lys
                100                 105

<210> SEQ ID NO 98
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: hu2F8 LCVR

<400> SEQUENCE: 98

Asp Ile Val Met Thr Gln Ser Pro Ser Ser Leu Ser Ala Ser Val Gly
 1               5                  10                  15

Asp Arg Val Thr Ile Thr Cys Lys Ala Ser Gln Asp Val Arg Thr Ala
                20                  25                  30

Val Ala Trp Tyr Gln Gln Lys Pro Gly Lys Ser Pro Lys Leu Leu Ile
             35                  40                  45

Ser Ser Thr Ser Tyr Arg Tyr Thr Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Tyr Ser Thr Pro Leu
                 85                  90                  95

Thr Phe Gly Gly Gly Thr Lys Val Glu Ile Lys
                100                 105

<210> SEQ ID NO 99
<211> LENGTH: 463
<212> TYPE: PRT
<213> ORGANISM: Artificial Sequence
<220> FEATURE:
<221> NAME/KEY: PEPTIDE
<222> LOCATION: (1)..(463)
<223> OTHER INFORMATION: huB7-H4-Fc

<400> SEQUENCE: 99

Phe Gly Ile Ser Gly Arg His Ser Ile Thr Val Thr Thr Val Ala Ser
 1               5                  10                  15

Ala Gly Asn Ile Gly Glu Asp Gly Ile Leu Ser Cys Thr Phe Glu Pro
                20                  25                  30

Asp Ile Lys Leu Ser Asp Ile Val Ile Gln Trp Leu Lys Glu Gly Val
             35                  40                  45

Leu Gly Leu Val His Glu Phe Lys Glu Gly Lys Asp Glu Leu Ser Glu
         50                  55                  60

Gln Asp Glu Met Phe Arg Gly Arg Thr Ala Val Phe Ala Asp Gln Val
 65                  70                  75                  80

Ile Val Gly Asn Ala Ser Leu Arg Leu Lys Asn Val Gln Leu Thr Asp
                 85                  90                  95

Ala Gly Thr Tyr Lys Cys Tyr Ile Ile Thr Ser Lys Gly Lys Gly Asn
                100                 105                 110

Ala Asn Leu Glu Tyr Lys Thr Gly Ala Phe Ser Met Pro Glu Val Asn
                115                 120                 125
```

Val Asp Tyr Asn Ala Ser Ser Glu Thr Leu Arg Cys Glu Ala Pro Arg
            130                 135                 140

Trp Phe Pro Gln Pro Thr Val Val Trp Ala Ser Gln Val Asp Gln Gly
145                 150                 155                 160

Ala Asn Phe Ser Glu Val Ser Asn Thr Ser Phe Glu Leu Asn Ser Glu
                165                 170                 175

Asn Val Thr Met Lys Val Val Ser Val Leu Tyr Asn Val Thr Ile Asn
                180                 185                 190

Asn Thr Tyr Ser Cys Met Ile Glu Asn Asp Ile Ala Lys Ala Thr Gly
                195                 200                 205

Asp Ile Lys Val Thr Glu Ser Glu Ile Lys Arg Arg Ser His Leu Gln
            210                 215                 220

Leu Leu Asn Ser Lys Ala Gly Ser Gly Gly Gly Gly Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
            290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
                340                 345                 350

Ser Lys Ala Lys Gly Gln Pro Arg Glu Pro Gln Val Tyr Thr Leu Pro
            355                 360                 365

Pro Ser Arg Asp Glu Leu Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
                435                 440                 445

His Asn His Tyr Thr Gln Lys Ser Leu Ser Leu Ser Pro Gly Lys
            450                 455                 460

```
<210> SEQ ID NO 100
<211> LENGTH: 276
<212> TYPE: PRT
<213> ORGANISM: Artificial Sequence
<220> FEATURE:
<221> NAME/KEY: PEPTIDE
<222> LOCATION: (1)..(276)
<223> OTHER INFORMATION: huB7-H4-his

<400> SEQUENCE: 100
```

Met Ala Ser Leu Gly Gln Ile Leu Phe Trp Ser Ile Ile Ser Ile Ile
1               5                   10                  15

```
Ile Ile Leu Ala Gly Ala Ile Ala Leu Ile Ile Gly Phe Gly Ile Ser
             20                  25                  30

Gly Arg His Ser Ile Thr Val Thr Thr Val Ala Ser Ala Gly Asn Ile
         35                  40                  45

Gly Glu Asp Gly Ile Leu Ser Cys Thr Phe Glu Pro Asp Ile Lys Leu
     50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                 85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Asp Tyr Lys Asp Asp Asp Lys Gly Ser His His His His His
            260                 265                 270

His His His His
        275

<210> SEQ ID NO 101
<211> LENGTH: 20
<212> TYPE: PRT
<213> ORGANISM: Homo sapiens

<400> SEQUENCE: 101

Thr Val Ala Ser Ala Gly Asn Ile Gly Glu Asp Gly Ile Leu Ser Cys
1               5                   10                  15

Thr Phe Glu Pro
            20

<210> SEQ ID NO 102
<211> LENGTH: 20
<212> TYPE: PRT
<213> ORGANISM: Artificial Sequence
<220> FEATURE:
<221> NAME/KEY: VARIANT
<222> LOCATION: (1)..(20)
<223> OTHER INFORMATION: antigen fragment P12 variant

<400> SEQUENCE: 102

Thr Val Ala Ser Ala Gly Asn Ile Gly Glu Asp Gly Ala Leu Ser Cys
1               5                   10                  15
```

```
Thr Phe Glu Pro
        20

<210> SEQ ID NO 103
<211> LENGTH: 20
<212> TYPE: PRT
<213> ORGANISM: Artificial Sequence
<220> FEATURE:
<221> NAME/KEY: VARIANT
<222> LOCATION: (1)..(20)
<223> OTHER INFORMATION: antigen fragment P12 variant

<400> SEQUENCE: 103

Thr Val Ala Ser Ala Gly Asn Ile Gly Glu Asp Gly Ile Ala Ser Cys
1               5                   10                  15

Thr Phe Glu Pro
        20

<210> SEQ ID NO 104
<211> LENGTH: 20
<212> TYPE: PRT
<213> ORGANISM: Artificial Sequence
<220> FEATURE:
<221> NAME/KEY: VARIANT
<222> LOCATION: (1)..(20)
<223> OTHER INFORMATION: antigen fragment P12 variant

<400> SEQUENCE: 104

Thr Val Ala Ser Ala Gly Asn Ile Gly Glu Asp Gly Ile Leu Ser Ala
1               5                   10                  15

Thr Phe Glu Pro
        20

<210> SEQ ID NO 105
<211> LENGTH: 20
<212> TYPE: PRT
<213> ORGANISM: Artificial Sequence
<220> FEATURE:
<221> NAME/KEY: VARIANT
<222> LOCATION: (1)..(20)
<223> OTHER INFORMATION: antigen fragment P12 variant

<400> SEQUENCE: 105

Thr Val Ala Ser Ala Gly Asn Ile Gly Glu Asp Gly Ile Leu Ser Cys
1               5                   10                  15

Ala Phe Glu Pro
        20

<210> SEQ ID NO 106
<211> LENGTH: 20
<212> TYPE: PRT
<213> ORGANISM: Artificial Sequence
<220> FEATURE:
<221> NAME/KEY: VARIANT
<222> LOCATION: (1)..(20)
<223> OTHER INFORMATION: antigen fragment P12 variant

<400> SEQUENCE: 106

Thr Val Ala Ser Ala Gly Asn Ile Gly Glu Asp Gly Ile Leu Ser Cys
1               5                   10                  15

Thr Ala Glu Pro
        20

<210> SEQ ID NO 107
<211> LENGTH: 20
```

```
<212> TYPE: PRT
<213> ORGANISM: Artificial Sequence
<220> FEATURE:
<221> NAME/KEY: VARIANT
<222> LOCATION: (1)..(20)
<223> OTHER INFORMATION: antigen fragment P12 variant

<400> SEQUENCE: 107

Thr Val Ala Ser Ala Gly Asn Ile Gly Glu Asp Gly Ile Leu Ser Cys
1               5                   10                  15

Thr Phe Ala Pro
            20

<210> SEQ ID NO 108
<211> LENGTH: 20
<212> TYPE: PRT
<213> ORGANISM: Artificial Sequence
<220> FEATURE:
<221> NAME/KEY: VARIANT
<222> LOCATION: (1)..(20)
<223> OTHER INFORMATION: antigen fragment P12 variant

<400> SEQUENCE: 108

Thr Val Ala Ser Ala Gly Asn Ile Gly Glu Asp Gly Ile Leu Ser Cys
1               5                   10                  15

Thr Phe Glu Ala
            20

<210> SEQ ID NO 109
<211> LENGTH: 7
<212> TYPE: PRT
<213> ORGANISM: Homo sapiens

<400> SEQUENCE: 109

Ile Leu Ser Cys Thr Phe Glu
1               5

<210> SEQ ID NO 110
<211> LENGTH: 5
<212> TYPE: PRT
<213> ORGANISM: Homo sapiens

<400> SEQUENCE: 110

Leu Ser Cys Thr Phe
1               5

<210> SEQ ID NO 111
<211> LENGTH: 8
<212> TYPE: PRT
<213> ORGANISM: Homo sapiens

<400> SEQUENCE: 111

Ile Leu Ser Cys Thr Phe Glu Pro
1               5
```